(12) United States Patent
Steinmetz et al.

(10) Patent No.: US 11,896,676 B2
(45) Date of Patent: Feb. 13, 2024

(54) TARGETING CANCER CELLS AND TISSUE USING FILAMENTOUS PLANT VIRUS PARTICLES

(71) Applicant: CASE WESTERN RESERVE UNIVERSITY, Cleveland, OH (US)

(72) Inventors: Nicole F. Steinmetz, San Diego, CA (US); Sourabh Shukla, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 498 days.

(21) Appl. No.: 16/988,210

(22) Filed: Aug. 7, 2020

(65) Prior Publication Data

US 2021/0038741 A1 Feb. 11, 2021

Related U.S. Application Data

(60) Provisional application No. 62/883,965, filed on Aug. 7, 2019.

(51) Int. Cl.
*A61K 47/69* (2017.01)
*A61K 47/10* (2017.01)
*A61K 45/06* (2006.01)

(52) U.S. Cl.
CPC .......... *A61K 47/6901* (2017.08); *A61K 47/10* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,004,606 | A | 4/1991 | Frincke |
| 2005/0019270 | A1 | 1/2005 | Finlay et al. |
| 2007/0248617 | A1 | 10/2007 | Bachmann et al. |
| 2007/0258889 | A1 | 11/2007 | Douglas et al. |
| 2007/0284545 | A1 | 12/2007 | Isacsson et al. |
| 2015/0033418 | A1 | 1/2015 | Lommel et al. |
| 2020/0179468 | A1* | 6/2020 | Steinmetz ............... A61P 35/04 |

FOREIGN PATENT DOCUMENTS

| | | |
|---|---|---|
| JP | 2009524699 A | 7/2009 |
| WO | 01/18199 A1 | 3/2001 |
| WO | 200118199 A1 | 3/2001 |
| WO | 2001/026682 A2 | 4/2001 |
| WO | 2003092623 A2 | 11/2003 |
| WO | 2012078069 A1 | 6/2012 |
| WO | 2013181557 A1 | 12/2013 |
| WO | 2014059021 A1 | 4/2014 |
| WO | 2015/0039255 A1 | 3/2015 |
| WO | 2015/188110 A1 | 12/2015 |
| WO | 2016019393 A1 | 2/2016 |
| WO | 2016/073972 A1 | 5/2016 |
| WO | 2016073972 A1 | 5/2016 |
| WO | 2016/149264 A1 | 9/2016 |
| WO | 2017/004123 A1 | 1/2017 |

OTHER PUBLICATIONS

Le, Duc et. al. Biodistribution of Filamentous Plant Virus Nanoparticles: Pepino Mosaic Virus versus Potato Virus X. Biomacromolecules. Jan. 14, 2019; 20(1): pp. 469-477. (Year: 2019).*
Le, Duc et al. Potato virus X, a filamentous plant viral nanoparticle for doxorubicin delivery in cancer therapy. Royal Society of Chemistry. Nanoscale, 2017 (9). pp. 2348-2357. (Year: 2017).*
Le, Duc et. al. Chemical addressability of potato virus X for its applications in bio/nanotechnology. El Sevier. Journal of Structural Biology 200 (2017). pp. 360-368. (Year: 2017).*
Czapar, Anna et. al. Tobacco Mosaic Virus Delivery of Phenanthriplatin for Cancer therapy. American Chemical Society. Nano 2016 (10) pp. 4119-4126. (Year: 2016).*
Tran, Hong Hanh. Developing a plant virus-based expression system for the expression of vaccines against Porcine Reproductive and Respiratory Syndrome Virus. Western Graduate & Postdoctoral Studies. Electronic Thesis and Dissertation Repository. (Year: 2017).*
"CWRU researcher to turn plant virus shells against human cancers", The Daily, CWRU Researcher to Turn Plant Virus Shells Against Human Cancers. Case Western Reserve University, Apr. 18, 2016.
Alaa A. Al. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.
Applicant: Case Western Reserve University; "Cancer Immunotherapy Using Virus Particles"; Canadian Office Action, dated Aug. 4, 2020; 3 pgs.
Applicant: Case Western Reserve University; "Plant Virus Particles for Delivery of Antimitotic Agents"; Extended European Search Report; dated Aug. 25, 2020; 11 pgs.
Canan Uluog, et al.: "Intermediate dose of methotrexate toxicity in non-Hodgkin lymphoma", General Pharmacology, vol. 32, 1999, pp. 215-218, XP55711259.
Chariou, et al., "Detection and Imaging of Aggressive Cancer Cells Using an Epidermal Growth Factor Receptor (EGFR)-Targeted Filamentous Plant Virus-Based Nanoparticle", Bioconjug Chem. Feb. 18, 2015; 26(2): 262-269.
Chinese Patent Appl. No. 201580063662.6; Chinese Office Action; dated May 5, 2022; 3 pgs.
European Search Report for Patent Application No. 15857504.3-1111/3215520, dated May 7, 2018.
Francisco, Joseph A., et al.; "cAC10-vcMMAE, an anti-CD30-monomethyl auristatin E conjugate with potent and selective antitumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.
International Search Report for Application No. PCT/US15/59675 (2016).

(Continued)

*Primary Examiner* — Nghi V Nguyen
(74) *Attorney, Agent, or Firm* — TAROLLI, SUNDHEIM, COVELL & TUMMINO, LLP

(57) ABSTRACT

A pepino mosaic virus (PepMV) carrier comprising a PepMV particle that has been modified to carry an imaging agent or anticancer agent is described. The PepMV carrier can be used in a method of targeting cancer cells and tissue by administering it to a subject. Cancer tissue targeted by the PepMV carrier can be imaged using an imaging agent, or treated using an anticancer agent.

14 Claims, 11 Drawing Sheets

(56) References Cited

OTHER PUBLICATIONS

Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.

Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.

Lee et al. "Biodegradable Viral Nanoparticle/Polymer Implants Prepared via Melt-Processing", ACS Nano ePub Sep. 13, 2017 vol. 11 No. 9 pp. 8777-8780.

Lee et al., "PEGylation to Improve Protein Stability During Melt Processing", Macromol Biosci 1-43, 57-75, Oct. 2015 vol. 15 No. 10 pp. 1332-1337.

Lizotte, et al., "Plant-derived viral-like nanoparticle immunotherapy suppress development of metastatic lung cancer", Journal of Immunology, vol. 194, Issue 1 Supplement, May 2015; 4 pgs.

Matsuura et al. Self-assembly of Ni-NT A-modified [3-annulus peptides into artificial viral capsids and encapsulation of His-tagged proteins. Org. Biomol. Chem., 2016, 14, 7869. DOI: 10.1039/c6ob01227b (Year: 2016).

Miermont et al., "Cowpea Mosaic Virus Capsid: A promising Carrier for the Development of Carbohydrate Based Antitumor Vaccines", Chem. Eur. J., 2008, vol. 14, pp. 4939-4947.

Nicole F. Steinmetz; U.S. Appl. No. 16/347,503, filed May 3, 2019; NonFinal Rejection dated Jun. 15, 2022; 36 pgs.

Nicole F. Steinmetz; U.S. Appl. No. 16/614,676, filed Nov. 18, 2019; NonFinal Rejection dated Jun. 3, 2022; 28 pgs.

Office action for Chinese Patent Application No. 201580063662.6, dated Mar. 4, 2020.

Office action for European Patent Application No. 15 857 504.3-1111, dated Mar. 18, 2020.

Office action for Japanese Patent Application No. 2017-524349, drafted Jan. 31, 2020; dated Feb. 10, 2020; 6 pgs.

Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].

Plchova et al. Expression of Human papillomavirus 16 E7ggg oncoprotein on N- and C-terminus of Potato virus X coat protein in bacterial and plant cells. Protein Expression and Purification 77 (2011); p. 146-152.

Sheen et al., "Stimulating Antitumor Immunity with Nanoparticles", Wiley Interdiscip Rev Nanomed Nanobiotechnol, Oct. 2014, vol. 6, pp. 496-505.

Smyth et al. Treatment of rapidly growing K-BALB and CT26 mouse tumours using Semliki Forest virus and its derived vector. Gene Therapy (2005) 12, 147-159.

Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.

Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.

Wen et al. Design of virus-based nanomaterials for medicine, biotechnology, and energy. Chem. Soc. Rev., 2016, 45, 4074. DOI: 10.1039/c5cs00287g (Year: 2016).

Yildiz, et al., "Applications of viral nanoparticles in medicine", Current Opinion in Biotechnology, vol. 22, Issue 6, (2011); pp. 901-908.

Applicant: Case Western Reserve University; "Cancer Immunotherapy Using Virus Particles"; Office Action, dated Aug. 4, 2020; 3 pgs.

Applicant: Case Western Reserve University; "Plant Virus Particles for Delivery of Antimitotic Agents"; Extended European Search Report; dated Aug. 17, 2020; 11 pgs.

Applicant: Case Western Reserve University; "Cancer Immunotherapy Using Virus Particles"; European Patent Application No. 18764856.3 for Supplementary European Search Report dated Dec. 22, 2020; 8 pgs.

Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.

Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.

Nicole F.Steinmetz; "Viral Nanoparticle Multimers"; U.S. Appl. No. 14/761,444, filed Jul. 16, 2015; Final Office Action dated Mar. 11, 2021; 11 pgs.

Agrawal Arpita et al: "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012 pp. 3320-3326, XP002780313.

Applicant: Case Western Reserve University; "Cancer Immunotherapy Using Virus Particles"; European Patent Application No. 21201960.8; Extended European Search Report dated Jan. 19, 2022; 11 pgs.

Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.

Gonzalez Maria J et al: "Interaction of Cowpea Mosaic Virus (CPMV) Nanoparticles with Antigen Presenting Cells In Vitro and In Vivo", PLOS ONE, vol. 4, No. 11, Nov. 2009 (Nov. 2009), XP002780311, ISSN: 1932-6203.

Patrick h. lizotte: "Novel approaches to targeting innate immunity for cancer Immunotherapy", Proquest Dissertations Publishing, May 2015 (May 2015), XP002780316, Retrieved from the Internet: URL:https://search.proquest.com/docview/16 95832154?pq-origsite=gscholar [retrieved on Apr. 19, 2018].

Saunders K et al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].

Office action for Japanese Patent Application No. 2017-524349, dated Jan. 31, 2020.

Yildiz et al., "Applications of viral nanoparticles in medicine", Current Opinion in Biotechnology, vol. 22, Issue 6, pp. 901-908.

Aljabali, et al., "CPMV-DOX Delivers", Molecular Pharmaceutics, 2013, 10, pp. 3-10.

Wen, et al., "Interior Engineering of a Viral Nanoparticle and its Tumor Homing Properties" Macromolecules, vol. 13, No. 12, Dec. 2012.

Agrawal, et al., "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012.

Brennan, et al., "Cowpea Mosaic Virus as a Vaccine Carrier of Heterologous Antigens", Molecular Biotechnology, vol. 17, No. 1, Jan. 2001.

Gonzalez, et al., "Interaction of Cowpea Mosaic Virus (CPMV) Nanoparticles with Antigen Presenting Cells in Vitro and In Vivo", PLOS ONE, vol. 4, No. 11, Nov. 2009.

Lizotte, et al., "Plant-derived viral-like nanoparticle immunotherapy suppress development of metastatic lung cancer", Journal of Immunology, vol. 194, Issue 1 Supplement, May 2015.

Patrick H. Lizotte, "Novel approaches to targeting innate immunity for cancer immunotherapy", Proquest Dissertations Publishing, May 2015.

Supplementary European Search Report for Patent Application No. 15857504.3-1111/3215520, dated May 28, 2018.

International Search Report for Application No. PCT/US15/59675.

(56) References Cited

OTHER PUBLICATIONS

Plchova et al. Expression of Human papillomavirus 16 E7ggg oncoprotein on N- and C-terminus of Potato virus X coat protein in bacterial and plant cells. Protein Expression and Purification 77 (2011

A  PepMV

Fig. 1A

B  PVX

Fig. 1B

TARGETING CANCER CELLS AND TISSUE USING FILAMENTOUS PLANT VIRUS PARTICLES

GOVERNMENT FUNDING

This invention was made with government support under Grant Nos. R00EB009105, P30EB011317, P30CA043703, and T32EB007509, P30CA043703, R01CA154656, R21CI81875, and UL1TR000439, R01CA202814, awarded by The National Institutes of Health and the National Science Foundation. The United States government has certain rights to the invention.

TECHNICAL FIELD

This application relates to pepino mosaic virus carriers and to their use in compositions for targeting, imaging, and treating cancer.

BACKGROUND

The next generation of nanotechnology-based imaging agents and drugs offers new opportunities in both fundamental and clinical research. State-of-the-art chemistries allow the fabrication of nanoparticles with a diverse portfolio of shapes and sizes, enabling the development of designer nanoparticles suitable for many different applications. While small molecule therapeutics and contrast agents suffer from poor solubility, rapid clearance, and nonspecific tissue distribution, nanoparticles have the potential to overcome these shortcomings. However, novel platforms are required to facilitate effective drug delivery and imaging beyond applications in cell culture and animal models. Although polymeric nanoparticles and liposomal drug formulations have received significant attention, biological nanomaterials offer advantages such as the biomanufacturing and self-replication of biological systems, leading to high-precision nanotechnologies.

The ability of nanoparticles to carry large drug payloads and the ease with which ligands can be added so that the payload is delivered to specific target sites (e.g. cancer or cardiovascular disease) make them particularly promising for biomedical applications. The chemical composition and physical properties of nanomaterials, such as shape and elasticity can significantly impact their fates in vivo. Recent studies indicate that filamentous nanomaterials have superior pharmacokinetic and tumor-homing properties. Decuzzi et al., Journal of Controlled Release 141, 320-327 (2010).

Viral nanoparticles (VNPs) are simple nanoscale structures consisting of a genome and a proteinaceous coat that is self-assembled from coat proteins (CPs). Programmed by nature, these nanostructures are diverse in terms of size (10-500 nm) and shape (icosahedrons, rods, filaments, or more complex head-to-tail architectures). Their advantages include homogeneity and monodispersity, resulting in a high degree of quality control that is critical for clinical translation. Several VNPs are currently being developed for nanomedical applications, where the vast majority of platforms under investigation are of spherical nature, e.g. the Human papilloma virus (HPV)-based Gardasil vaccine, and Adenovirus-based gene-delivery vectors.

Plant VNPs are biocompatible, biodegradable, and non-infectious in mammals and can be produced in large quantities by molecular farming with high yields and excellent reproducibility. Various spherical plant viruses including Cowpea mosaic virus (CPMV), Brome mosaic virus (BMV), Cowpea chlorotic mottle virus (CCMV), Hibiscus chlorotic ringspot virus (HCSRV), and Red clover necrotic mottle virus (RCNMV).

As the vast majority of platform technologies currently under development consist of spherical or elongated low aspect ratio materials (AR<5), few high aspect ratio VNPs have been investigated. Those that have, including Tobacco mosaic virus (TMV) and bacteriophage M13, have focused mainly on in vitro tissue engineering applications. Pokorski, J. K. and N. F. Steinmetz. Mol Pharm 8(1): 29-43 (2011). However, more recently soft-matter nanotubes formed by TMV have also been used for drug delivery, imaging, vaccine development and cancer immunotherapy. Similarly, the filamentous particles formed by the Potato virus X (PVX) have been explored for the same broad panel of applications.

Physically and chemically tailoring materials at the nanoscale in two dimensions to create high aspect ratio materials is challenging using synthetic materials, mainly due to polydispersity and poorly controlled chemistry. Efforts in synthetic chemistry and nanotechnology have sought to mimic characteristics, such as self-assembly and programmability at the atomic level that nature has already achieved. Therefore, a bio-inspired approach to engineer additional viral nanoparticles (VNPs) from plants for imaging and drug delivery is desirable as each platform has shown to be different in terms of its material properties, chemistry, suitability for engineering and in vivo fate.

SUMMARY

Embodiments described herein relate to pepino mosaic virus (PepMV) carriers and there use in the imaging and treatment of cancer. The filamentous plant virus carriers can include a PepMV particle that has been modified to carry an imaging agent or cytotoxic compound. In further embodiments, the PepMV virus species carrier is PEGylated to reduce immunogenicity. In additional embodiments, PEGylation is also used to enhance stability and pharmacokinetics.

Additional embodiments relate to methods of targeting cancer tissue in a subject, by administering to the subject a PepMV carrier comprising a PepMV particle modified to carry an imaging agent or a cytotoxic compound such as an antitumor agent. An imaging agent can include a fluorescent molecule for fluorescent imaging. In some embodiments, the cancer tissue is ovarian or breast cancer. In particular embodiments, the cancer tissue is triple negative breast cancer tissue. In further embodiments, the PepMV carrier is administered together with a pharmaceutically acceptable carrier.

Other embodiments described herein relate to methods of treating cancer in a subject. The method includes administering to the subject a therapeutically effective amount of PepMV carrier comprising a PepMV particle modified to carry an anticancer agent, such as a cytotoxic compound. In some embodiments, the cancer tissue is ovarian cancer or breast cancer tissue. In particular embodiments, the cancer tissue is triple negative breast cancer tissue. In further embodiments, the PepMV carrier is administered together with a pharmaceutically acceptable carrier.

DETAILED DESCRIPTION

Figure 1C:
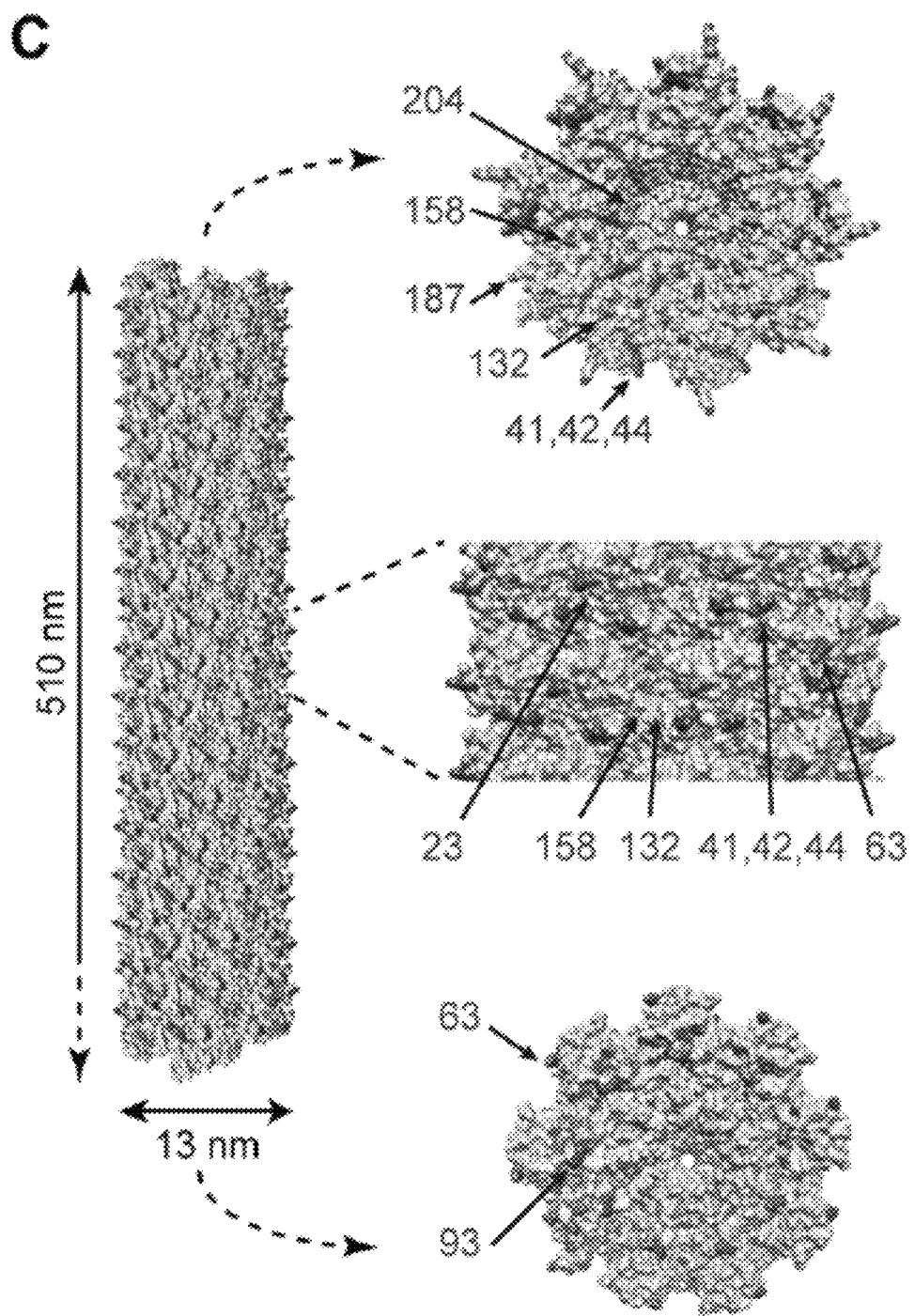
FIGS. 1(A-F) illustrate images showing structural models of PepMV and PVX. The atomic models of (A) PepMV and (B) PVX coat protein (CP) subunits highlighting lysine side chains (Lys, green). Representation of a portion of the helical assemblies of (C) PepMV and (D) PVX CP (300 subunits). Views from different angles (top view, side view, and bottom view) indicate surface-exposed Lys. Surface electrostatic potentials of the atomic structures of (E) PepMV and (F) PVX. Negatively charged, neutral, and positively charged surfaces are shown.
Figure 1D:
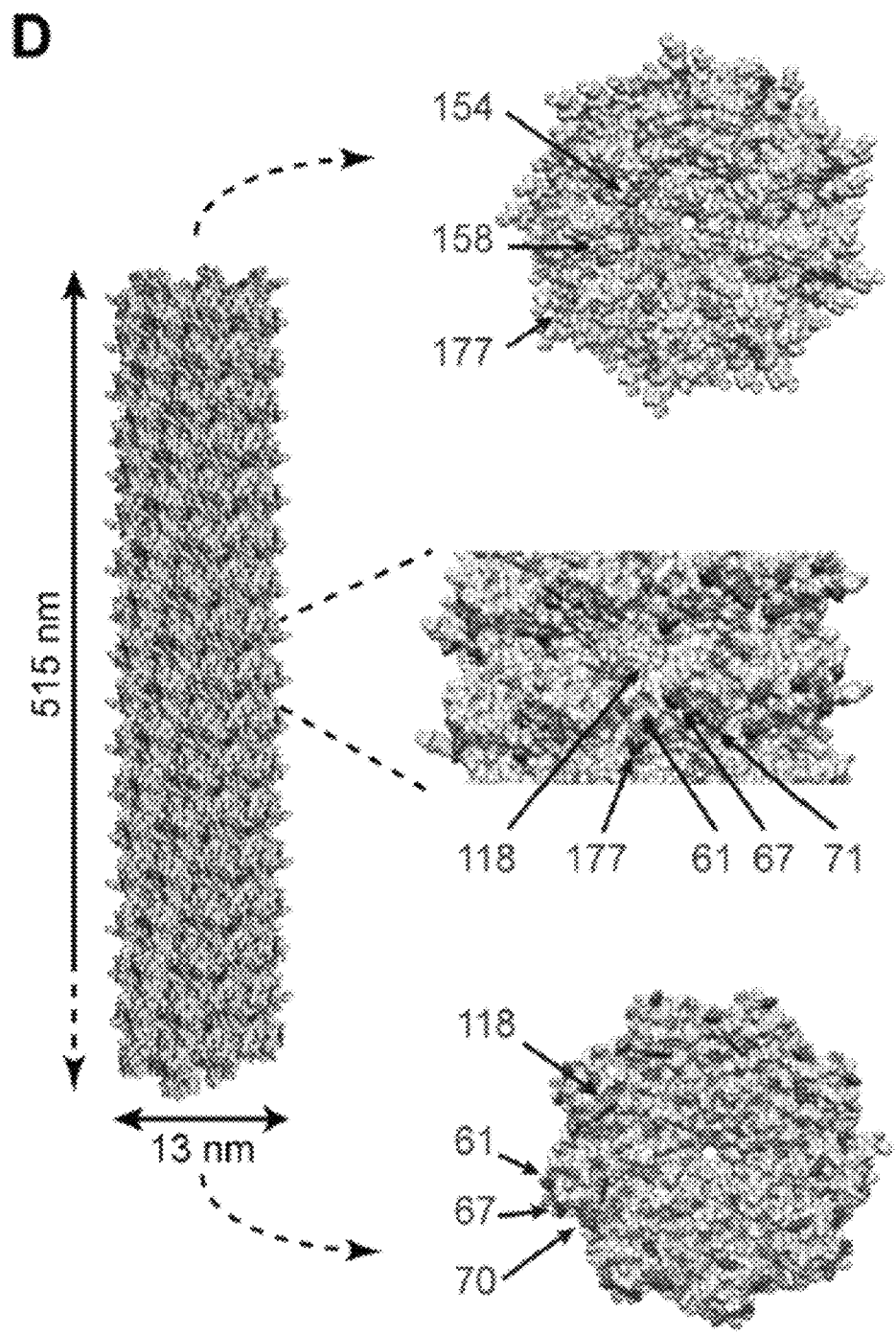

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994.

All scientific and technical terms used in this application have meanings commonly used in the art unless otherwise specified. The definitions provided herein are to facilitate understanding of certain terms used frequently herein and are not meant to limit the scope of the application. Although any methods and materials similar or equivalent to those described herein can be used in the practice for testing of the present invention, the preferred materials and methods are described herein. In describing and claiming the present invention, the following terminology will be used.

As used in this specification and the appended claims, the singular forms "a", "an" and "the" include plural references unless the content clearly dictates otherwise. Thus, for example, reference to "a cell" includes a combination of two or more cells, and the like. In addition, the recitations of numerical ranges by endpoints include all numbers subsumed within that range (e.g., 1 to 5 includes 1, 1.5, 2, 2.75, 3, 3.80, 4, 5, etc.).

The terms "comprise," "comprising,", "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably. Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "or" as used herein should be understood to mean "and/or", unless the context clearly indicates otherwise.

As used in this specification and the appended claims, the singular forms "a", "an" and "the" include plural references unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

"Image" or "imaging" refers to a procedure that produces a picture of an area of the body, for example, organs, bones, tissues, or blood.

"Treat", "treating", and "treatment", etc., as used herein, refer to any action providing a benefit to a subject afflicted with a condition or disease such as cancer, including improvement in the condition through lessening or suppression of at least one symptom, delay in progression of the disease, etc.

"Prevention", as used herein, refers to any action providing a benefit to a subject at risk of being afflicted with a condition or disease such as cancer, including avoidance of the development of cancer or a decrease of one or more symptoms of the disease should cancer develop. The subject may be at risk due to exposure to a carcinogen, or as a result of family history.

A "subject," as used herein, can be any animal, and may also be referred to as the patient. Preferably, the subject is a vertebrate animal, and more preferably, the subject is a mammal, such as a domesticated farm animal (e.g., cow, horse, pig) or pet (e.g., dog, cat). In some embodiments, the subject is a human.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent, which will achieve the goal of decreasing disease severity, e.g., cancer, while avoiding adverse side effects such as those typically associated with alternative therapies. The therapeutically effective amount may be administered in one or more doses.

A "therapeutic" treatment is a treatment administered to a subject who exhibits signs of pathology of a disease or disorder for the purpose of diminishing or eliminating those signs.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

"Targeting," as used herein, refers to the ability of PepMV carriers to be delivered to and preferentially accumulate in cancer tissue in a subject. As used herein, the term "targeting agent" can refer to a molecule or molecules that are able to bind to and complex with a biomarker. The term can also refer to a functional group that serves to target or direct PepMV carriers to a particular location, cell type, diseased tissue, or association. In general, a "targeting agent" can be directed against a biomarker.

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

The terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

The term "nanoparticle" refers to any particle having a diameter of less than 1000 nanometers (nm). In general, the nanoparticles should have dimensions small enough to allow their uptake by eukaryotic cells. Typically, the nanoparticles have a longest straight dimension (e.g., diameter) of 200 nm or less. In some embodiments, the nanoparticles have a diameter of 100 nm or less. Smaller nanoparticles, e.g., having diameters of 50 nm or less, e.g., about 1 nm to about 30 nm or about 1 nm to about 5 nm, are used in some embodiments.

The phrases "parenteral administration" and "administered parenterally" are art-recognized terms and include modes of administration other than enteral and topical administration, such as injections, and include, without limitation, intratumoral, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion. In certain embodiments, the PepMV carrier is systemically or intraperitoneally administered.

The phrases "systemic administration," "administered systemically," "peripheral administration" and "administered peripherally" as used herein mean the administration of a compound, agent or other material other than directly into a specific tissue, organ, or region of the subject being treated (e.g., tumor site), such that it enters the animal's system and, thus, is subject to metabolism and other like processes, for example, subcutaneous administration.

Embodiments described herein relate to PepMV carriers and there use in the imaging and treatment of cancer.

PepMV is a common pathogen that infects tomato plants. Pharmaceutical scale production of PepMV vectors can be achieved using a stable PepMV vector. PepMV, like PVX, belongs to the genus Potexvirus in the family Flexiviridae. The filamentous nucleoprotein architectures are assembled from helically arranged CP subunits around the single-stranded, positive-sense RNA. PepMV virions are constructed from 1290 identical CPs to form a 510×13 nm filament similar to the 515×13 nm PVX virion having 1270 identical CPs.

It was found that PepMV particles can be conjugated to small molecule modifiers, including fluorescent probes and therapeutic agents, via the amine groups of surface exposed Lys residues to yield viral nanoparticles capable of carrying up to about 1600 modifiers per particle. In addition, it was discovered that PepMV carriers including PepMV particles described herein can achieve significantly enhanced tumor homing with less nonspecific tissue distribution compared to potato virus X (PVX) in mouse models of ovarian and breast cancer. Without being bound by theory, it is believed that the distinct amino acid compositions of PepMV and PVX lead to subtle differences in the surface chemistry resulting in the enhanced tumor homing of PepMV compared to PVX.

Accordingly, in some embodiments, a PepMV particle can be modified to allow conjugation of an imaging agent or cytotoxic compound. Conjugating an imaging agent or a cytotoxic compound to the PepMV particle allows the PepMV particle to function as a targeted imaging agent or a targeted cytotoxic agent. A PepMV particle that has been modified to include an imaging agent or a cytotoxic compound is also referred to herein as a PepMV carrier.

In some embodiments, the PepMV particles include a nucleic acid within the virus particle. If present, the nucleic acid will typically be the nucleic acid encoding the virus. However, in some embodiments the viral nucleic acid may have been replaced with exogenous nucleic acid. A virus particle including nucleic acid will still be nonreplicating and noninfectious when it is introduced into a subject, which it cannot infect. For example, PepMV particles will typically be nonreplicating and noninfectious when introduced into an animal subject. In other embodiments, the PepMV can be a virus like protein (VLP). VLPs are self-assembled structures derived from viral antigens that mimic the native architecture of viruses but lack the viral genome. VLPs lacking their nucleic acid are non-replicating and non-infectious regardless of the subject into which they are introduced.

The PepMV particles can be obtained according to various methods known to those skilled in the art. Plant virus particles such as PepMV preferably grow in plants where the virus particles can be obtained from the extract of a plant infected by the plant virus. Within a week or two after infection, leaves are harvested and viral nanoparticles are extracted. Procedures for obtaining plant virus particles using extraction of an infected plant are known to those skilled in the art. See Wellink J., Meth Mol Biol, 8, 205-209 (1998). Procedures are also available for obtaining virus-like particles. Saunders et al., Virology, 393(2):329-37 (2009). The disclosures of both of these references are incorporated herein by reference.

Plant virus particles such as PepMV have the advantages of being readily cultivated, and are unlikely to cause infection when used in vivo in a subject. In planta production prevents endotoxin contamination that may be a byproduct of other virus particle systems derived from *E. coli*. The PepMV particles are scalable, stable over a range of temperatures (4-60° C.) and solvent:buffer mixtures. In an exemplary embodiment, PepMV can be propagated in *Nicotiana benthamiana* plants and then purified. Typically, 100 g of infected leaves can yield about 10 to about 20 mg of PepMV.

In general, imaging agents and/or cytotoxic compounds (collectively referred to herein as agents) can be conjugated to the PepMV by any suitable technique, with appropriate consideration of the need for pharmacokinetic stability and reduced overall toxicity to the patient. The term "conjugating" when made in reference to an agent and a PepMV particle as used herein means covalently linking the agent to the virus subject to the single limitation that the nature and size of the agent and the site at which it is covalently linked to the virus particle do not interfere with the biodistribution of the modified virus.

An agent can be coupled to a PepMV particle either directly or indirectly (e.g. via a linker group). In some embodiments, the agent is directly attached to a functional group capable of reacting with the agent. PepMV has multiple surface-exposed lysine residues that can be targeted to display up to about 1600 small chemical modifiers (e.g., biotin or Cy5) per particle. For example, PepMV viral coat proteins (CPs) include lysines that have a free amino group that can be capable of reacting with a carbonyl-containing group, such as an anhydride or an acid halide, or with an alkyl group containing a good leaving group (e.g., a halide). In addition, genetic modification can be applied to introduce any desired functional residue, including non-natural amino acids, e.g. alkyne- or azide-functional groups. See Pokorski, J. K. and N. F. Steinmetz Mol Pharm 8(1): 29-43 (2011).

Alternatively, a suitable chemical linker group can be used. A linker group can serve to increase the chemical reactivity of a substituent on either the agent or the virus particle, and thus increase the coupling efficiency. A preferred group suitable for attaching agents to the virus particle are lysine residues present in the viral coat protein.

Suitable linkage chemistries include maleimidyl linkers, alkyl halide linkers and succinimidyl (e.g., N-hydroxysuccinimidyl (NHS)) linkers (which react with a primary amine on the PepMV particle). Several primary amine groups are present on viral coat proteins, and additional groups can be designed into recombinant viral coat proteins. It will be evident to those skilled in the art that a variety of bifunctional or polyfunctional reagents, both homo- and heterofunctional (such as those described in the catalog of the Pierce Chemical Co., Rockford, Ill.), can be employed as a linker group. Coupling can be effected, for example, through amino groups, carboxyl groups, sulfhydryl groups or oxidized carbohydrate residues. In an exemplary embodiment, the PepMV particles and biotin-NHS can be mixed at a 1:1 CP/biotin ratio overnight at room temperature in 10 mM KP buffer (pH 7.0) containing 10% (v/v) DMSO and purified using 100 kDa molecular weight cutoff spin filters. In another exemplary embodiment, the PepMV particles and Cy5-NHS can be mixed at a 1:1, 1:2, 1:5, 1:10 or 1:20 CP/Cy5-NHS ratio overnight at room temperature and purified using ultracentrifugation.

Other types of linking chemistries are also available. For example, methods for conjugating polysaccharides to peptides are exemplified by, but not limited to coupling via alpha- or epsilon-amino groups to NaIO4-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide linker wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, for example where a cytotoxic moiety is more potent when free from the targeting/imaging molecules, it can be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710); by irradiation of a photolabile bond (e.g., U.S. Pat. No. 4,625,014); by hydrolysis of derivatized amino acid side chains (e.g., U.S. Pat. No. 4,638,045); by serum complement-mediated hydrolysis (e.g., U.S. Pat. No. 4,671,958); and acid-catalyzed hydrolysis (e.g., U.S. Pat. No. 4,569,789).

It can be desirable to couple more than one cytotoxic and/or imaging moiety to a PepMV particle of the invention. By poly-derivatizing the PepMV particle of the invention, several cytotoxic strategies can be simultaneously implemented. For example, a PepMV virus carrier can be made useful as a contrasting agent for several visualization techniques, or a PepMV virus carrier including a cytotoxic agent can be labeled for tracking by a visualization technique. In one embodiment, multiple molecules of a cytotoxic compound are coupled to a PepMV particle. In another embodiment, more than one type of cytotoxic compound can be coupled to a PepMV particle.

In some embodiments, the PepMV particle is modified to carry an imaging agent; i.e., the PepMV carrier comprises an imaging agent to track the particles and image the tumor being imaged and/or treated. Examples of imaging agents include fluorescent, radioactive isotopes, MRI contrast agents, enzymatic moieties, or detectable label of the invention. For example, in some embodiments, the imaging agent is a fluorescent molecule for fluorescent imaging. The detectable group can be any material having a detectable physical or chemical property. Such detectable labels have been well developed in the field of fluorescent imaging, magnetic resonance imaging, positive emission tomography, or immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, AlexaFluor555, Texas red, rhodamine, and the like), radiolabels (e.g., $^{3}H$, $^{14}C$, $^{35}S$, $^{125}I$, $^{121}I$, $^{112}In$, $^{99}mTc$), other imaging agents such as microbubbles (for ultrasound imaging), $^{18}F$, $^{11}C$, $^{15}O$, (for Positron emission tomography), $^{99}mTC$, $^{111}In$ (for Single photon emission tomography), gadolinium chelate or iron (for magnetic resonance imaging), enzymes (e.g., horse radish peroxidase, alkaline phosphatase and others commonly used in an ELISA), and calorimetric labels such as colloidal gold or colored glass or plastic (e.g. polystyrene, polypropylene, latex, and the like) beads.

In some embodiments, the imaging agent includes a fluorescent dye. Exemplary Fluorescent dyes include fluorescein isothiocyanate, cyanines such as Cy5, Cy5.5 and analogs thereof (e.g., sulfo-Cyanine 5 NHS ester and Cy5.5 maleimide). In a particular embodiment, PepMV is conjugated to Cy5 fluorescent dye. See also Handbook of Fluorescent Probes and Research Chemicals, 6th Ed., Molecular Probes, Inc., Eugene Oreg., which is incorporated herein by reference.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include compounds of the Alexa Fluor® series (Invitrogen™), fluorescein and its derivatives, rhodamine and its derivatives, dansyl, umbelliferone, and the like Chemiluminescent compounds include luciferin, and 2,3-dihydrophthalazinediones, e.g., luminol. For a review of various labeling or signal producing systems, which may be used, see, U.S. Pat. No. 4,391,904, incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple calorimetric labels may be detected simply by observing the color associated with the label.

In certain embodiments of the invention, the PepMV particles can be coupled or conjugated to one or more anticancer agents. In some embodiments, the anticancer agent is a cytotoxic compound that inhibits cell growth or promotes cell death when proximate to or absorbed by a cell. Suitable cytotoxic compounds in this regard include radioactive agents or isotopes (radionuclides), chemotoxic agents such as differentiation inducers, inhibitors and small chemotoxic drugs, toxin proteins and derivatives thereof, as well as nucleotide sequences (or their antisense sequence). Therefore, the cytotoxic compound can be, by way of non-limiting example, an antitumor agent, a photoactivated toxin or a radioactive agent.

Preferred radionuclides for use as cytotoxic compounds are radionuclides, which are suitable for pharmacological administration. Such radionuclides include $^{123}I$, $^{125}I$, $^{131}I$, $^{90}Y$, $^{211}At$, $^{67}Cu$, $^{186}Re$, $^{188}Re$, $^{212}Pb$, and $^{212}Bi$. Iodine and astatine isotopes are more preferred radionuclides for use in the therapeutic compositions of the present invention, as a large body of literature has been accumulated regarding their use. $^{131}I$ is particularly preferred, as are other β-radiation emitting nuclides, which have an effective range of several millimeters. $^{123}I$, $^{125}I$, $^{131}I$, or $^{211}At$ can be conjugated to filamentous viral particles for use in the compositions and methods utilizing any of several known conjugation reagents, including Iodogen, N-succinimidyl 3-[211At]astatobenzoate, N-succinimidyl 3-[131I]iodobenzoate (SIB), and, N-succinimidyl 5-[131I]iodo-3-pyridinecarboxylate (SIPC). Any iodine isotope can be utilized in the recited iodo-reagents. Other radionuclides can be conjugated to the PepMV particles by suitable chelation agents known to those of skill in the nuclear medicine arts.

Cytotoxic compounds for use in a PepMV carrier described herein can include small-molecule antitumor agents. Examples of antitumor agents include, but are not limited to, angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, phenanthriplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin, and derivatives thereof.

In some embodiments, antitumor agents can be directly conjugated to the PepMV particle via a chemical linker, or can be encapsulated in a carrier, which is in turn coupled to the PepMV particle.

In further embodiments, the anticancer agent is a platinum-based anticancer agent. Platinum-based anticancer agents include both neutral (platinum(II)) and cationic (platinum(IV)) platinum-based anticancer agents. Examples of neutral platinum-based anticancer agents include cisplatin, carboplatin, oxaliplatin, nedaplatin, and lobaplatin, which are in a sense more traditional platinum-based anticancer compounds. Cationic platinum-based anticancer agents include a variety of compounds such as satraplatin, picoplatin, and phenanthriplatin. In certain embodiments, the cationic platinum-based anticancer agent is phenanthriplatin. For additional platinum(IV) anticancer agents, see Lovejoy, K, and Lippard, S., Dalton Trans. 48, 10651-10659 (2009) and Zheng et al., JACS, 136, 8790-8798 (2014), the disclosures of which are incorporated herein by reference.

Preferred toxin proteins for use as cytotoxic compounds include ricin, abrin, diphtheria toxin, cholera toxin, gelonin, *Pseudomonas* exotoxin, *Shigella* toxin, pokeweed antiviral protein, and other toxin proteins known in the medicinal biochemistry arts. As these toxin agents can elicit undesirable immune responses in the patient, especially if injected intravascularly, it is preferred that they be encapsulated in a carrier for coupling to the PepMV particles.

In some embodiments, a coating can be added to the exterior of the PepMV particle to improve bioavailability. Administering the PepMV carrier to a subject can generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Generation of an immune response by the PepMV carrier is typically undesirable. Accordingly, in some embodiments it may be preferable to modify the PepMV carrier or take other steps to decrease the immune response. For example, an immunosuppressant compound can be administered to decrease the immune response. More preferably, the PepMV carrier can be modified to decrease its immunogenicity. Examples of methods suitable for decreasing immunity include attachment of anti-fouling (e.g., zwitterionic) polymers, glycosylation of the virus carrier, and PEGylation.

In some embodiments, the immunogenicity of the PepMV carrier is decreased by PEGylation. PEGylation is the process of covalent attachment of polyethylene glycol (PEG) polymer chains to a molecule such as a filamentous plant virus carrier. PEGylation can be achieved by incubation of a reactive derivative of PEG with the filamentous plant virus carrier. The covalent attachment of PEG to the PepMV carrier can "mask" the agent from the host's immune system, and reduce production of antibodies against the carrier. PEGylation also may provide other benefits. PEGylation can be used to vary the circulation time of the PepMV carrier. For example, use of PEG 5,000 can provide a virus carrier with a circulation half-life of about 12.5 minutes, while use of PEG 20,000 can provide a virus carrier with a circulation half-life of about 110 minutes.

The first step of PEGylation is providing suitable functionalization of the PEG polymer at one or both terminal positions of the polymer. The chemically active or activated derivatives of the PEG polymer are prepared to attach the PEG to the PepMV carrier. There are generally two methods that can be used to carry out PEGylation; a solution phase batch process and an on-column fed-batch process. The simple and commonly adopted batch process involves the mixing of reagents together in a suitable buffer solution, preferably at a temperature between 4 and 6° C., followed by the separation and purification of the desired product using a chromatographic technique.

An additional advantage to PEGylating the PepMV particles is that PEGylation provides a convenient means for attaching additional compounds such as ligands for a tumor-associated receptor. For example, EGFR ligands can be conjugated to a PepMV particle via PEG spacers to enhance tissue-specificity and targeted delivery.

In some embodiment, a method of using a PepMV particle to target cancer tissue in a subject is provided. The method includes administering a PepMV carrier including a PepMV particle modified to carry an imaging agent or a cytotoxic compound to the subject. As defined herein, targeting cancer tissue can refer to the ability of the PepMV particles to reach and preferably accumulate within cancer tissue after being administered to the subject. The ability of PepMV carriers including PepMV particles to target cancer tissue is supported by the biodistribution studies described herein. While not intending to be bound by theory, it appears that the tumor homing after systemic administration results from the enhanced permeability and retention (EPR) effect in solid tumors where tumor hypervascularzation results in gaps between endothelial cells allowing the extravasation of nanoscale objects, i.e. the PepMV particles. It is further believed that the lack of lymphatic drainage leads to the retention of PepMV particles at the tumor site and that PepMV can evade phagocytosis and thus have prolonged circulation times, leading to more efficient tumor accumulation.

In some embodiments, the PepMV carriers described herein are used to treat or image cancer tissue selected from the group consisting of breast and ovarian cancer. In certain embodiments, the PepMV carriers described herein are used to treat or image triple negative breast cancer tissue.

In some embodiments, the method also includes the step of imaging the cancer tissue in the subject using an imaging device subsequent to administering an effective amount of the PepMV carrier to the subject. Examples of imaging methods include computed tomography, positive emission tomography, and magnetic resonance imaging.

"Computed tomography (CT)" refers to a diagnostic imaging tool that computes multiple x-ray cross sections to produce a cross-sectional view of the vascular system, organs, bones, and tissues. "Positive emissions tomography (PET)" refers to a diagnostic imaging tool in which the patient receives a radioactive isotopes by injection or ingestion which then computes multiple x-ray cross sections to produce a cross-sectional view of the vascular system, organs, bones, and tissues to image the radioactive tracer. These radioactive isotopes are bound to compounds or drugs that are injected into the body and enable study of the physiology of normal and abnormal tissues. "Magnetic resonance imaging (MRI)" refers to a diagnostic imaging tool using magnetic fields and radiowaves to produce a cross-sectional view of the body including the vascular system, organs, bones, and tissues.

Another aspect of the invention provides a method of treating cancer in a subject by administering a therapeutically effective amount of a PepMV carrier including a PepMV particle modified to carry an imaging agent or a cytotoxic compound. In some embodiments, the therapeutically effective amount is the amount required to decrease a tumor volume in a subject.

As used herein, PepMV carriers including a PepMV particle modified to carry an imaging agent or a cytotoxic compound can reach and preferably accumulate within cancer tissue after being administered to the subject. The ability of plant virus particles themselves to target cancer tissue is supported by the biodistribution studies carried out by the inventors. For additional support, see International Patent Publication WO2013/181557. The disclosure of which is incorporated herein by reference.

In some embodiments, the PepMV particle can provide additional anticancer activity in addition to the anticancer effects of a conjugated anticancer agent, such as a cytotoxic compound. While not intending to be bound by theory, this additional anticancer therapy appears to be the result of an immunotherapeutic effect of the PepMV particle themselves.

PepMV carriers or PepMV particles alone described herein can be used to treat a variety of different types of cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

The cancers treated by a method described herein can include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, glioblastoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, fallopian tube cancer, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In particular embodiments, the PepMV carriers including a PepMV particle described herein are used to treat a cancer selected from the group consisting of breast cancer, and ovarian cancer.

In certain embodiments, the cancer treated is triple negative breast cancer. Triple negative breast cancer is a breast cancer where the three most common types of receptors known to fuel most breast cancer growth—estrogen, progesterone, and the HER-2/neu gene—are not present in the cancer tumor. This means that the breast cancer cells have tested negative for hormone epidermal growth factor receptor 2 (HER-2), estrogen receptors (ER), and progesterone receptors (PR). Since the tumor cells lack the necessary receptors, common treatments like hormone therapy and drugs that target estrogen, progesterone, and HER-2 are ineffective.

In some embodiments, in addition to administering a PepMV carrier, the method of treating cancer in a subject can further include the step of administering a therapeutically effective amount of a cancer therapeutic or cancer therapy to the subject. A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy.

In some embodiments, the method can further include the step of administering a therapeutically effective amount of an anticancer therapeutic agent to the subject. The anticancer therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA. In some embodiments, cytotoxic compounds are included in an anticancer agent described herein. Cytotoxic compounds include small-molecule drugs such as doxorubicin, mitoxantrone, methotrexate, and pyrimidine and purine analogs, referred to herein as antitumor agents.

The anticancer therapeutic agent can include an anticancer or an antiproliferative agent that exerts an antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Non-limiting exemplary anticancer therapeutic agents that can be administered in combination with a plant virus or virus-like particle described herein include Taxol, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; temozolomide, teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Still other anticancer therapeutic agents include alkylating agents, such as nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.), antimetabolites, such as folic acid analog (e.g., methotrexate), or pyrimidine analogs (e.g., fluorouracil, floxouridine, Cytarabine), purine analogs (e.g., mercaptopurine, thioguanine, pentostatin, vinca alkaloids (e.g., vinblastin, vincristine), epipodophyllotoxins (e.g., etoposide, teniposide), platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, amino glutethimide).

In particular embodiments, anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin, rapamycin, thapsigargin, and bikunin, and derivatives (as defined for imaging agents) thereof.

In some embodiments, a method of treating cancer described herein can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins.

In some embodiments, the step of ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g., IL-2, interferon's, cytokine inducers).

In contrast, specific cancer immunotherapy is based on certain antigens that are preferentially or solely expressed on cancer cells or predominantly expressed by other cells in the context of malignant disease (usually in vicinity of the tumor site). Specific cancer immunotherapy can be grouped into passive and active approaches.

In passive specific cancer immunotherapy substances with specificity for certain structures related to cancer that are derived from components of the immune system are administered to the patient. The most prominent and successful approaches are treatments with humanized or mouse/human chimeric monoclonal antibodies against defined cancer associated structures (such as Trastuzumab, Rituximab, Cetuximab, Bevacizumab, Alemtuzumab). The pharmacologically active substance exerts is activity as long as a sufficient concentration is present in the body of the patient, therefore administrations have to be repeated based on pharmacokinetic and pharmacodynamic considerations.

On the other hand, active specific cancer immunotherapy aims at antigen-specific stimulation of the patient's immune system to recognize and destroy cancer cells. Active specific cancer immunotherapy therefore, in general, is a therapeutic vaccination approach. There are many types of cancer vaccine approaches being pursued, such as vaccination with autologous or allogeneic whole tumor cells (in most cases genetically modified for better immune recognition), tumor cell lysates, whole tumor associated antigens (produced by means of genetic engineering or by chemical synthesis), peptides derived from protein antigens, DNA vaccines encoding for tumor associated antigens, surrogates of tumor antigens such as anti-idiotypic antibodies used as vaccine antigens, and the like. These manifold approaches are usually administered together with appropriate vaccine adjuvants and other immunomodulators in order to elicit a quantitatively and qualitatively sufficient immune response (many novel vaccine adjuvant approaches are being pursued in parallel with the development of cancer vaccines). Another set of cancer vaccine approaches relies on manipulating dendritic cells (DC) as the most important antigen presenting cell of the immune system. For example, loading with tumor antigens or tumor cell lysates, transfection with genes encoding for tumor antigens and in vivo targeting are suitable immunotherapies that can be used together with the PepMV carriers of the invention for cancer treatment.

In some embodiments related to administering a PepMV carrier for the treatment of triple negative breast cancer in a subject, the method can include the step of administering an additional cancer therapeutic or cancer therapy to the subject specific for the treatment of triple negative breast cancer. For example, triple negative breast cancer is typically treated using one or more therapeutics or therapies including chemotherapeutics, conservative breast surgery, radiation therapy and non-HER2 targeted therapy.

Chemotherapeutic agents for the treatment of triple negative breast cancer can include anthracycline, taxanes (e.g., paclitaxel), antimetabolites, platinum agents and microtubule stabilizing agents (e.g., ixabepilone). Antimetabolites for the treatment of triple negative breast cancer can include capecitabine or a combination of capecitabine and vinorelbine, or gemcitabine and vinorelbine. Exemplary platinum agents can include cisplatin or carboplatin. Platinum-based regimens can further include combinations of cisplatin plus gemcitabine, carboplatin plus paclitaxel and carboplatin plus gemcitabine, and carboplatin plus and EGFR inhibitor, such as cetuximab.

Targeted therapies for the treatment of triple negative breast cancer can include PARP-1 inhibitors such as BSI-201 and olaparib. Additional targeted therapies for the treatment of triple negative breast cancer can include, but are not limited to: EGFR inhibitors such as cetuximab, panitumumab, gefitinib, afatinib and erlotinib; FGFR2 inhibitors such as dovitinib (TKI258), lucitanib (E-3810), BGJ398, JNJ-42756493, and AZD4547; VEGF inhibitors such as bevacizumab; and mTOR inhibitors such as everolimus.

The methods described herein include administering to a subject, preferably a mammal, and more preferably a human, the PepMV carrier or additional agent of the invention in an amount effective to produce the desired effect. In some embodiments, the PepMV carrier is administered together with a pharmaceutically acceptable carrier to provide a pharmaceutical formulation. The PepMV carrier may be present in a pharmaceutical composition in an amount from 0.001 to 99.9 wt %, more preferably from about 0.01 to 99 wt %, and even more preferably from 0.1 to 95 wt %.

Pharmaceutically acceptable carriers enable the PepMV carrier to be delivered to the subject in an effective manner while minimizing side effects, and can include a variety of diluents or excipients known to those of ordinary skill in the art. Formulations include, but are not limited to, those suitable for oral, rectal, vaginal, topical, nasal, ophthalmic, or parental (including subcutaneous, intramuscular, intraperitoneal, intratumoral, and intravenous) administration. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

In certain embodiments, such as for the treatment of ovarian cancer, formulations for local delivery via an intraperitoneal (i.p.) route are preferred. Ovarian cancer primary and metastatic tumors are frequently restricted to the peritoneal cavity and therefore i.p. injection can allow for direct exposure to PepMV carriers and/or additional agents described herein leading to increased tumor exposure and PepMV carrier accumulation in tumors as well as reduced clearance rates.

A pharmaceutically acceptable carrier for a pharmaceutical composition can also include delivery systems known to the art for entraining or encapsulating drugs, such as anti-cancer drugs. In some embodiments, the disclosed compounds can be employed with such delivery systems including, for example, liposomes, nanoparticles, nanospheres, nanodiscs, dendrimers, and the like. See, for example Farokhzad, O. C., Jon, S., Khademhosseini, A., Tran, T. N., Lavan, D. A., and Langer, R. (2004). "Nanoparticle-aptamer bioconjugates: a new approach for targeting prostate cancer cells." Cancer Res., 64, 7668-72; Dass, C. R. (2002). "Vehicles for oligonucleotide delivery to tumours." J. Pharm. Pharmacol., 54, 3-27; Lysik, M. A., and Wu-Pong, S. (2003). "Innovations in oligonucleotide drug delivery." J. Pharm. Sci., 92, 1559-73; Shoji, Y., and Nakashima, H. (2004). "Current status of delivery systems to improve target efficacy of oligonucleotides." Curr. Pharm. Des., 10, 785-96; Allen, T. M., and Cullis, P. R. (2004). "Drug delivery systems: entering the mainstream." Science, 303, 1818-22. The entire teachings of each reference cited in this paragraph are incorporated herein by reference.

The formulations may be conveniently presented in unit dosage form and may be prepared by any of the methods well known in the art of pharmacy. Preferably, such methods include the step of bringing the PepMV carrier into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention including a PepMV carrier in an amount effective to produce the desired effect. The formulated PepMV carrier can be administered as a single dose or in multiple doses.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose.

Single or multiple administrations of the compositions may be administered depending on the dosage and frequency as required and tolerated by the subject. In both prophylactic and therapeutic regimes, agents are usually administered in several dosages until an effect has been achieved. A pharmaceutically acceptable composition containing the PepMV carrier, PepMV particle, and/or additional cancer therapeutic can be administered at regular intervals, depending on the nature and extent of the cancer's effects, and on an ongoing basis. Administration at a "regular interval," as used herein, indicates that the therapeutically effective amount is administered periodically (as distinguished from a one-time dose). In one embodiment, the pharmaceutically acceptable composition including the PepMV carrier, and/or an additional cancer therapeutic is administered periodically, e.g., at a regular interval (e.g., bimonthly, monthly, biweekly, weekly, twice weekly, daily, twice a day or three times or more often a day).

The administration interval for a single individual can be fixed, or can be varied over time, depending on the needs of the individual. For example, in times of physical illness or stress, or if disease symptoms worsen, the interval between doses can be decreased.

For example, the administration of a PepMV carrier, PepMV particle, and/or the additional therapeutic agent can take place at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least once on week 1, 2, 3, 4, 5, 6, 7, 8, 9, 10, 11, 12, 13, 14, 15, 16, 17, 18, 19 or 20, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g., between 6:00 a.m. and 12:00 noon; in the afternoon, e.g., after noon and before 6:00 p.m.; or in the evening, e.g., between 6:01 p.m. and midnight.

Effective doses of the PepMV carrier vary depending upon many different factors, including means of administration, target site, physiological state of the patient, whether the patient is human or an animal, other medications administered, and whether treatment is prophylactic or therapeutic. In any event, the administration regime should provide a sufficient quantity of PepMV carrier of this invention to effectively treat the subject.

For administration for targeting or imaging in a mammalian subject utilizing a PepMV carrier, the dosage of the imaging or cytotoxic agent ranges from about 0.0001 to 100 mg/kg, and more usually 0.01 to 50 mg/kg, of the host body weight. For example dosages can be 1 mg/kg body weight or 10 mg/kg body weight or within the range of 1-10 mg/kg. A suitable amount of virus particle is used to provide the desired dosage. In an exemplary embodiment, a PepMV carrier is administered to a subject at a dose of about 10 mg/kg body weight.

An exemplary treatment regime entails administration once per every two weeks or once a month or once every 3 to 6 months. A suitable amount of PepMV carrier is used to provide the desired dosage. The PepMV carrier is usually administered on multiple occasions. Alternatively, the PepMV carrier can be administered as a sustained release formulation, in which case less frequent administration is required. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

The pharmaceutical compositions including a PepMV carrier can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). In some embodiments, the frequency of administration of a PepMV carrier can pose challenging for clinical implementation. Therefore, in some embodiments, the PepMV carrier is administered in situ to a subject and can be formulated in a slow release formulation in order to sustain a therapeutic concentration of the PepMV carrier in situ while alleviating the need for frequent administrations. In some embodiments, a slow release formulation can include a polymer-based hydrogel or a dendrimer.

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The present invention is illustrated by the following examples. It is to be understood that the particular examples, materials, amounts, and procedures are to be interpreted broadly in accordance with the scope and spirit of the invention as set forth herein.

Example

We previously found that filamentous PVX (515×13 nm) and icosahedral CPMV (30 nm) differ in their biodistribution profiles, with PVX demonstrating enhanced tumor homing and tissue penetration. These observations are matched with data from studies using synthetic nanomaterials such as carbon nanotubes and filomicelles, confirming that a high aspect ratio is advantageous for nanomedical applications because the particles evade phagocytosis, leading to prolonged circulation time while also exhibiting enhanced margination and extravasation thus facilitating homing and accumulation at tumor sites.

Here, we compared the properties of PVX and the Pepino mosaic virus (PepMV), a common pathogen that infects tomato plants. A stable PepMV vector was recently generated to support biomanufacturing. PepMV and PVX both belong to the genus Potexvirus in the family Flexiviridae. They share filamentous nucleoprotein architectures assembled from helically arranged CP subunits around their single-stranded, positive-sense RNAs. The PepMV virion is constructed from 1290 identical CPs to form a 510×13 nm filament very similar to the 515×13 nm PVX virion comprising 1270 identical CPs. The PVX particle offers addressable lysine (Lys) and cysteine (Cys) side chains, allowing the preparation of the multimodal nanotechnology platform. We used the available three-dimensional (3D) structural model of PepMV to identify chemically addressable Lys side chains and to establish bioconjugation procedures. We developed PepMV with small chemical modifiers such as a biotin tag and a fluorescent probe. The in vivo fate of fluorescence-labeled PepMV in terms of biodistribution and tumor homing properties was then compared in mouse models of triple negative breast cancer and ovarian cancer.

Materials and Methods

Preparation of the Filamentous VNPs

PepMV and PVX were propagated in *Nicotiana benthamiana* plants and purified according to our established protocols. The yields from 100 g of infected leaves were ~10 to 20 mg of pure PepMV and PVX.

Structural Models of the Filamentous VNPs

The atomic model and cryoEM structure of the PepMV CP were generated using UCSF Chimera with data imported from the Protein Data Bank (PDB 5FN1). The atomic model of the PVX CP (NCBI AAV27212.1) was constructed using the Rosetta web server by comparative modeling based on the PepMV atomic model. The PVX and PepMV CPs share 53% sequence similarity and 37% sequence identity. The assembled structure of PVX was generated by fitting the PepMV model in UCSF Chimera, assuming similar helical symmetry parameters. Addressable Lys was depicted in green from the top, side, and bottom of the VNP models. Surface charge densities were calculated using the Bluues server based on generalized Born radii.

Chemical Bioconjugation of the VNPs

Biotin N-hydroxysuccinimide ester (Biotin-NHS) and sulfo-Cyanine5 NHS (Cy5-NHS) were obtained from Medchem Express and Lumiprobe, respectively. For amine-NHS coupling, mixtures of VNPs (2 mg mL$^{-1}$) with the NHS reagents were prepared in 10 mM potassium phosphate (KP) buffer containing 10% (v/v) DMSO (pH 7.0). All reactions were carried out at room temperature overnight. Biotin-NHS was added at a 1:1 molar ratio with the CP. Cy5-NHS was added at increasing CP/dye ratios of 1:1, 1:2, 1:5, 1:10, and 1:20. Biotinylated PepMV and PVX were purified by 10 washes in 10 mM KP buffer, using 100-kDa molecular weight cutoff size exclusion spin filters. For fluorescence-labeled particles, the PepMV-Cy5 and PVX-Cy5 conjugates were purified by three rounds of ultracentrifugation (112,000×g, 1 h, 4° C.) over a 30% (w/v) sucrose cushion. The pellets were then resuspended in 10 mM KP buffer, pH 7.0.

Denaturing Gel Electrophoresis (SDS-PAGE)

Denatured samples (5 µg) were loaded onto 4-12% NuPAGE gels (Thermo Fisher Scientific) in 1×MOPS running buffer (Thermo Fisher Scientific). Electrophoresis was conducted at a constant voltage (200 V) for 35 min. Labeled samples were detected by excitation at 632 nm (red) and imaged using the FluoroChem R imaging instrument (ProteinSimple). After staining with Coomassie Blue (CB), protein bands were visualized under white light and imaged using the same equipment.

Western Blot (WB) Analysis

After SDS-PAGE, the separated capsid bands were then transferred from gels onto a nitrocellulose membrane (Thermo Fisher Scientific) and blocked for 60 min using 5% (w/v) skimmed milk powder dissolved in 0.1 M Tris-buffered saline containing 0.05% (v/v) Tween-20 (TBST). Alkaline phosphatase-conjugated streptavidin (Sigma-Aldrich) diluted in 5% (w/v) milk in TBST at a 1:500 ratio was used to detect the biotinylated samples. BCIP/NBT substrate for alkaline phosphatase was added for visualization. Imaging was carried out using the FluoroChem R imaging instrument.

Transmission Electron Microscopy (TEM) Imaging

Samples (0.1 mg mL-1) were loaded onto carbon-coated grids and negatively stained with 0.2% (w/v) uranyl acetate. Grids were imaged using a FEI Tecnai F30 transmission electron microscope operated at 300 kV.

Immunogold Staining for the Detection of Biotinylated VNPs

Samples loaded on carbon-coated grids were washed with 10 mM KP buffer and blocked with 1% (w/v) bovine serum albumin (BSA) containing 0.1% (v/v) Tween-20 for 30 min. After equilibration in 0.1% (w/v) BSA for 5 min, the samples were stained with 10 nm gold nanoparticles conjugated to antibiotin antibodies (AURION) diluted 5-fold in KP buffer. Finally, the samples were negatively stained using 2% (w/v) uranyl acetate for 1 min prior to TEM imaging using a FEI Tecnai F30 transmission electron microscope at 300 kV.

UV/Vis Spectroscopy

A Nanodrop 2000 spectrometer (Thermo Fisher Scientific) was used to measure the absorbance at 260 nm (for viral RNAs) to determine the VNP concentration and the absorbance at 647 nm to determine the concentration of attached dyes after purification. Using the Beer-Lambert law and extinction coefficients specific for PepMV (2.9 mL mg$^{-1}$ cm$^{-1}$), PVX (3.0 mL mg-$^1$ cm$^{-1}$), and Cy5 (271,000 M$^{-1}$ cm$^{-1}$), the molar ratios of conjugated dyes per particle were calculated. Triplicate samples were prepared, and data were expressed as means±SD. Statistical significance was determined by applying a t test in GraphPad Prism.

Biodistribution Studies

To track the filamentous VNPs in vivo, PepMV and PVX were labeled with Cy5 as above using CP/dye ratios for PepMV and PVX optimized at 1:0.4 and 1:1, respectively, ensuring ~300 dye molecules per particle in both cases. Purification was then carried out by two rounds of ultracentrifugation (212,000×g, 3 h, 4° C.). The filamentous structures of PepMV-Cy5 and PVX-Cy5 were confirmed by TEM before in vivo administration. All animal studies were conducted following the protocols and procedures approved by Case Western Reserve University's Institutional Animal Care and Use Committee (IACUC). Athymic female NCR nu/nu mice (6-8 weeks old, obtained from Case Western Reserve University) were fed on an alfalfa-free diet to reduce auto-fluorescence. For the triple negative breast cancer (TNBC) model, mice (6-8 weeks old) were injected subcutaneously in the right flank with 2×10$^6$ cells suspended in 100 µL 1:1 Matrigel/medium. Tumor volumes were monitored daily and calculated using the formula u=(1× w2)/2 where 1 is the length and w is the width of a tumor. Biodistribution was analyzed when the tumor volume reached 100-150 mm3. PepMV-Cy5 and PVX-Cy5 were administered intravenously at a dose of 10 mg kg-1 body weight. Mice were euthanized, and organs were collected for ex vivo imaging using the IVIS spectrum imaging system (PerkinElmer Ltd.) 24 h post injection. Regions of interest (ROI) were analyzed using the IVIS Living Image v4.2 (PerkinElmer Ltd.) to determine the fluorescence intensity per area from each organ. Data were expressed as means±SD (n=3). Similarly, for the ovarian cancer model, luciferase-positive SKOV-3/Luc cells ($2\times10^6$ cells in 0.2 mL PBS) were injected intraperitoneally (i.p.) and tumor growth was monitored weekly by bioluminescence imaging following the injection of D-luciferin (Thermo Fisher Scientific) at a dose of 150 mg $kg^{-1}$. The total luminescence intensity was determined by ROI analysis. After 40 days, mice were injected i.p. with PepMV-Cy5 and PVX-Cy5 at a dose of 10 mg $kg^{-1}$ body weight. The VNP distribution was monitored in vivo using the IVIS system under isoflurane anesthesia at defined time points for 72 h. Organs were collected and imaged ex vivo, and ROI analysis was conducted as described above. Quantitative data were expressed as means±SD (n=3).

Results

Mapping of Addressable Lys Side Chains on the Filamentous VNPs

To explore the available engineering design space of the VNPs, the three-dimensional (3D) structures of PepMV and PVX were constructed using UCSF Chimera software (FIG. 1). The PepMV and PVX CP atomic models with all Lys side chains (amino groups highlighted in green) are shown in parts A and B of FIG. 1, respectively. The corresponding assembled nanoparticles are shown in parts C and D of FIG. 1, respectively, illustrating the surface-exposed Lys from different angles. In addition, the electrostatic potentials of the solvent-exposed surfaces on each VNP were calculated using the Bluues server, indicating that each assembled CP featured a negatively charged surface (FIGS. 1E, F). There are 13 Lys residues in the PepMV CP and 11 in the PVX CP, as shown in parts A and B of FIG. 1, respectively. The structural model of PepMV (FIG. 1C), viewed from the side, indicates that Lys 41, 42, 44, 63, and 18 are fully exposed (Lys 18 is not shown; the first 20 residues are solvent-exposed but not included in the atomic models because the lack of electron density indicates a flexible structure). Lys 23, 132, and 158 are partially buried in the surface, and Lys 93, 187, and 204 face the CP interfaces and are therefore only exposed at the ends. Finally, Lys 150 and 196 are buried in the CP structure (FIG. 1C). The PVX structural model indicates five fully exposed Lys residues (20, 61, 67, 71, and 177) as well as the partially exposed Lys 118 (FIG. 1D). Lys 154 and 158 face the CP interfaces and are therefore exposed only at the end structures of the PVX virion (FIG. 1D). The structural data thus indicate that both PepMV and PVX have several solvent-exposed Lys side chains.

Bioconjugation of PepMV and PVX

Figure 2A:
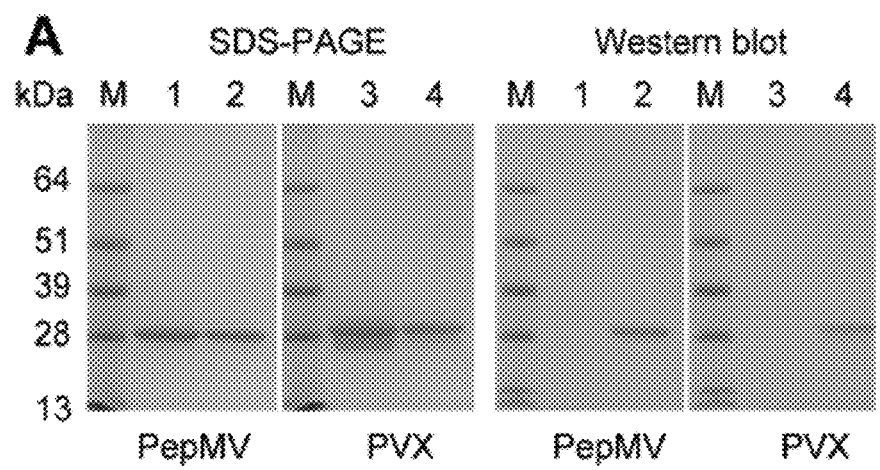
FIGS. 2(A-C) illustrate immunoblots and images showing characterization of PepMV-biotin and PVX-biotin conjugates. (A) Gel electrophoresis (SDS-PAGE) and Western blot analysis of (1) PepMV control vs (2) PepMV-biotin, (3) PVX control vs (4) PVX-biotin. M: See Blue Plus2 Protein Standards. (B, C) TEM images of immunogold stained (B) non-modified PepMV and PepMVbiotin and (C) nonmodified PVX and PVX-biotin. Scale bars=100 nm.
Figure 2B:
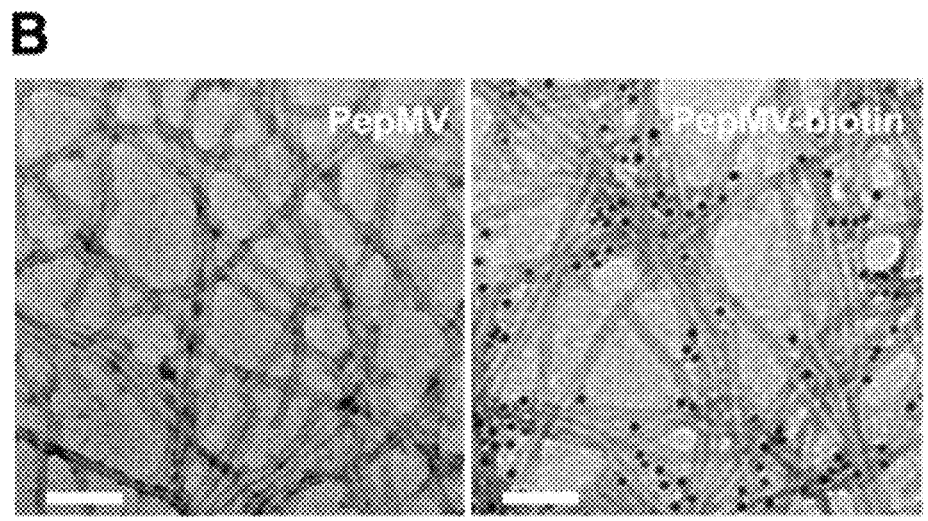
Figure 2C:
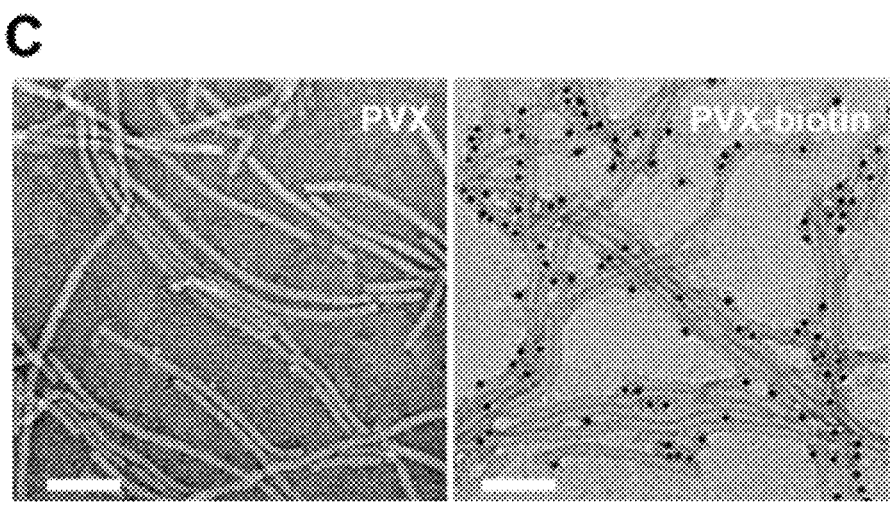
Figure 3A:
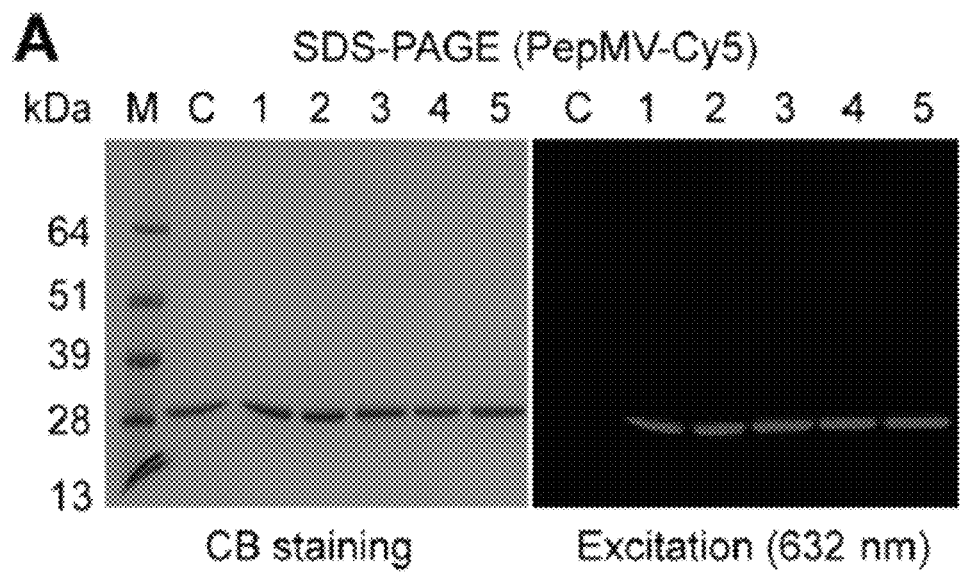
FIGS. 3(A-D) illustrate immunoblots, images, and a plot showing characterization of fluorescence-labeled PepMV-Cy5 and PVX-Cy5. SDS-PAGE analysis of (A) PepMV-Cy5 and (B) PVX-Cy5 at increasing molar excesses of sulfo-Cy5-NHS in the reaction mixtures. (1-5) CP/dye molar ratio: 1:1, 1:2, 1:5, 1:10, 1:20, C/nonlabeled particles as controls. (C) The filamentous structures of PepMV-Cy5 and PVX-Cy5 after modification and purification. Scale bars=100 nm. (D) The number of attached Cy5 molecules per particle (PepMV or PVX) as a function of the molar excess of dye. Experiments were carried out in triplicate, values are shown as means±SD. Error bars are not displayed when their length is smaller than the marker sizes.
Figure 3B:
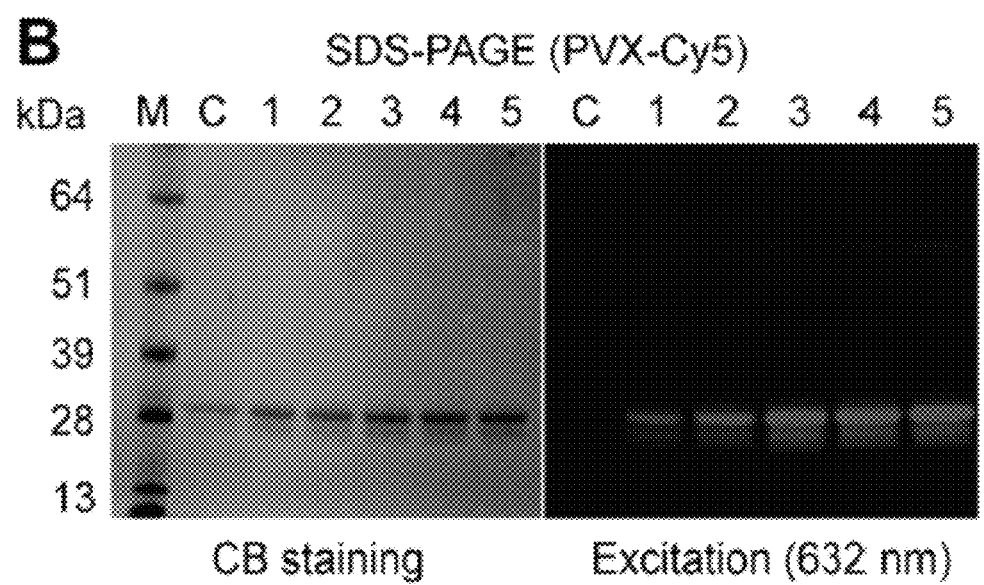
Figure 3C:
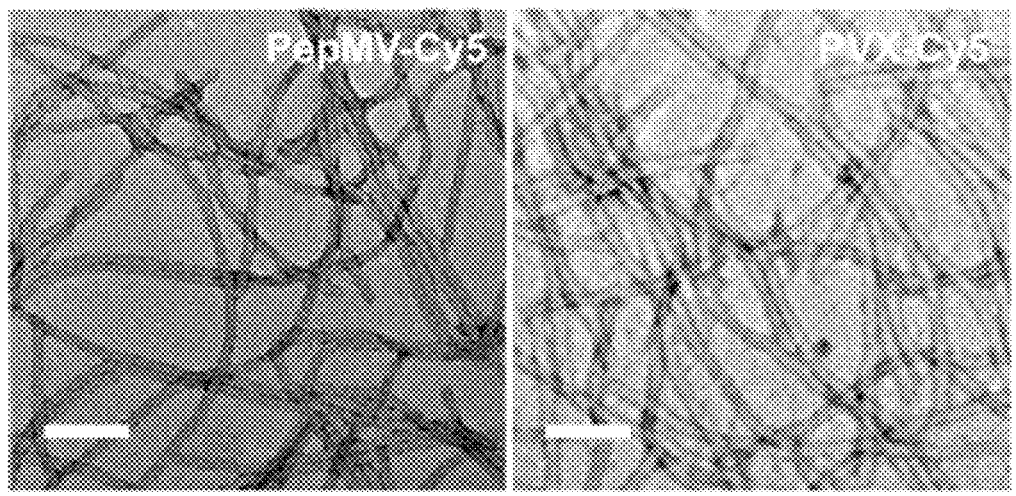
Figure 3D:
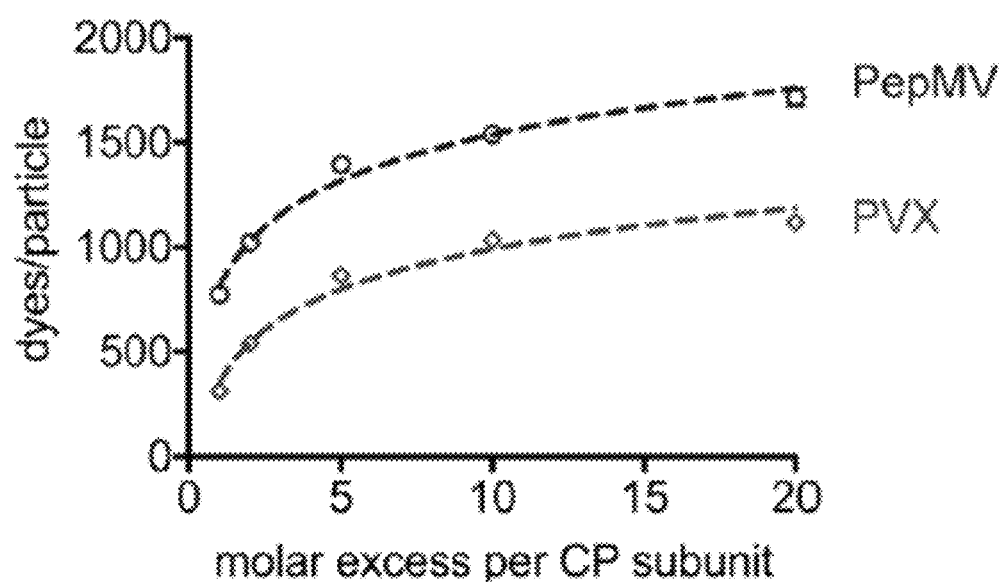
Figure 6:
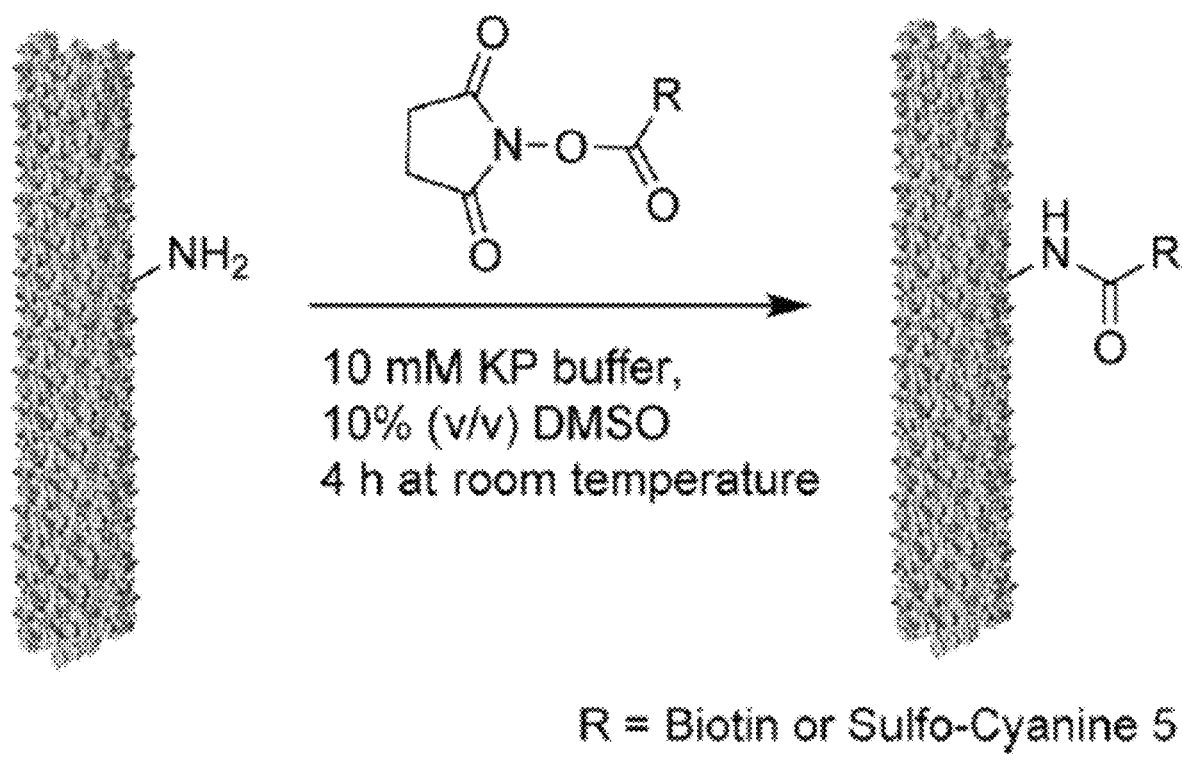
FIG. 6 illustrates a reaction scheme for the bioconjugate of PepMV or PVX with a Biotin Tag or the fluorescent probe Cy5 functionalized with the NHS-Handle via an Amine-NHS coupling reaction.

Next, we compared the versatility of PepMV and PVX by testing a series of bioconjugation chemistries (FIGS. 2 and 3). We previously demonstrated that PVX could be labeled on solvent-exposed Lys side chains with small chemical modifiers using Nhydroxysuccinimide (NHS) esters. Up to 1600 modifiers (e.g., Oregon green 488) could be displayed per particle, indicating that each of the 1270 identical CP copies could accommodate one or two conjugated molecules. Here, we used similar bioconjugation procedures to test the chemistry of PepMV, namely NHS esters of biotin and sulfo-Cyanine 5 fluorophores (FIG. 6).

First, we tested the biotinylation of Lys side chains on the filamentous VNPs (FIG. 2). PepMV or PVX suspensions at a final concentration of 2 mg mL-1 were mixed with biotin-NHS at a 1:1 CP/biotin-NHS ratio in 10 mM KP buffer (pH 7.0) containing 10% (v/v) DMSO at room temperature overnight. The biotinylated conjugates (PepMV-biotin and PVX-biotin) were then purified using 100 kDa molecular weight cutoff spin filters (10 washes with 10 mM KP buffer) to remove excess biotin. SDS-PAGE and Western blot analysis confirmed the successful biotinylation of both viruses (FIG. 2A). SDSPAGE revealed a ~25 kDa band representing the PepMV and PVX CP, but no increase in molecular weight was observed following the conjugation reaction due to the small size of biotin (244 Da). Nevertheless, Western blots probed with alkaline phosphatase-conjugated streptavidin confirmed the presence of the biotin tag. Immunogold-TEM imaging using an antibiotin antibody conjugated with 10 nm gold nanoparticles also confirmed that PepMV and PVX were coated with biotin and that the VNPs preserved their flexuous, filamentous structures after bioconjugation and purification, as shown in parts B and C of FIG. 2.

Next, we used a fluorescent label (sulfo-Cyanine 5 NHS, Cy5-NHS) to quantify the loading capacity of PepMV (FIG. 3). PepMV and PVX particle suspensions (2 mg $mL^{-1}$) were mixed with Cy5-NHS at 1:1, 1:2, 1:5, 1:10, and 1:20 CP/Cy5-NHS ratios. The reactions were carried out at room temperature overnight, followed by three rounds of ultracentrifugation (112,000×g, 1 h, 4° C.) to remove excess dye. After SDS-PAGE, the gels were first visualized by excitation at 632 nm (red) to detect conjugated Cy5 (Ex/Em 647/662 nm) (FIGS. 3A, B). In contrast to the nonmodified CPs, the Cy5-conjugated CPs were fluorescent, indicating that both PepMV and PVX were successfully labeled (FIGS. 3A, B). TEM imaging confirmed that PepMV and PVX (prepared using a Cy5-NHS/CP ratio of 1:1) remained intact after the labeling and purification procedure (FIG. 3C). Next, we determined the number of Cy5 dye molecules attached per PepMV or PVX particle by UV/vis spectroscopy using the Beer-Lambert law and the specific extinction coefficients of PepMV (2.9 mL $mg^{-1}$ $cm^{-1}$ at 260 nm), PVX (3.0 mL mg-1 cm-1 at 260 nm), and Cy5 (271,000 $M^{-1}$ $cm^{-1}$ at 647 nm). As shown in FIG. 3D, more dye molecules are conjugated as the molar excess of dye increases. The reaction reached a plateau with conjugation efficiencies of 1600 Cy5 per PepMV and 1100 Cy5 per PVX using the 1:20 CP/Cy5-NHS ratio. Under each condition tested, PepMV showed a higher loading capacity than PVX ($p<0.001$, t test in GraphPad Prism). The slightly higher loading capacity of PepMV may reflect the larger number of solvent-exposed Lys side chains that are accessible during the conjugation reaction.

Biodistribution Studies

Figure 4A:
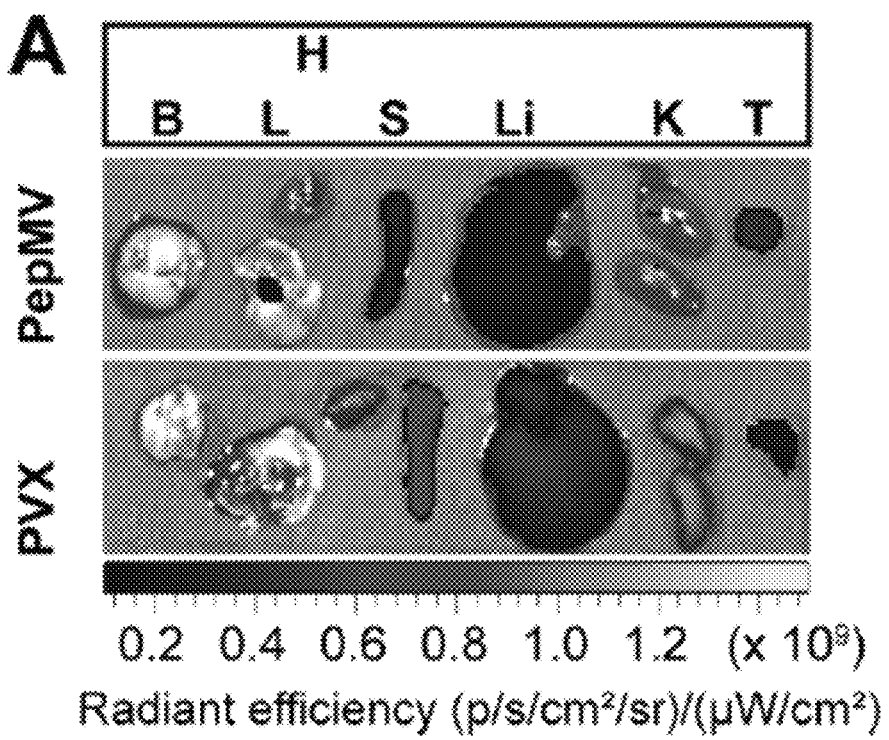
FIGS. 4(A-B) illustrate images and a plot showing biodistribution profiles of PepMV and PVX 24 h post intravenous administration at a dose of 10 mg/kg in nu/nu mice bearing MDAMB-231 triple negative breast cancer tumors. (A) Ex vivo fluorescence images of excised organs. (B) Quantitative region of interest (ROI) analysis of each organ determined by total radiant efficiency per area. Data are expressed as means±SD (n=3).

To investigate the potential of PepMV for drug delivery and/or diagnostic imaging applications, we carried out biodistribution studies using two mouse models: a nu/nu mouse model of TNBC using subcutaneously inoculated MDA-MB-231 cells and a model of ovarian cancer using intraperitoneally inoculated SKOV-3 cells. All animal studies were conducted according to Case Western Reserve University IACUC-approved protocols. To monitor the nanoparticles in vivo and ex vivo, PepMV-Cy5 and PVX-Cy5 were prepared using reaction conditions that ensured each particle was labeled with ~300 dye molecules, which is suitable for imaging without quenching effects. Free dye was removed by ultracentrifugation, and the integrity of the filamentous particles was confirmed by TEM before injection. The number of PepMV and PVX particles in animal tissues was determined indirectly by measuring the fluorescence intensity. PepMV-Cy5 and PVX-Cy5 (10 mg kg-1 body weight) were administered intravenously (i.v.) to female mice bearing MDA-MB-231 tumors or intraperitoneally (i.p.) to mice bearing SKOV-3 tumors. In vivo and ex vivo imaging was performed using an IVIS spectrum imaging system, followed by the quantitative analysis of fluorescence in each organ (ROI analysis) using Living Imaging Software (FIGS. 4 and 5). One-way analysis of variance (ANOVA) in GraphPad Prism was used to determine the statistical significance of differences between tissues, and t tests were similarly used for pairwise comparisons between PepMV and PVX in each tissue.

Figure 4B:
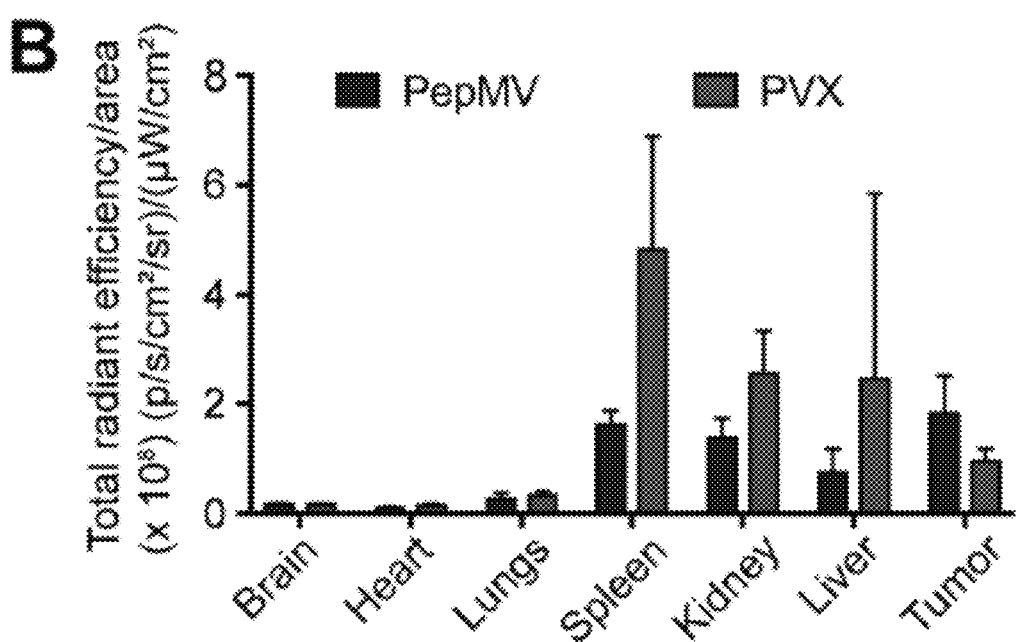

For the TNBC model, MDA-MB-231 cells were inoculated subcutaneously at a concentration of $2\times10^6$ cells mL-1 in the right flank of female nu/nu mice. After 14 days, when tumor volumes reached 100-150 mm$^3$, mice were divided into two groups for the i.v. injection of PepMV-Cy5 and PVX-Cy5, respectively. The mice were euthanized 24 h post injection for ex vivo imaging (FIG. 4A), followed by quantitative ROI analysis of the collected organs (FIG. 4B). The biodistribution profiles of PepMV and PVX were similar, with particle accumulation in the liver, spleen, and kidney. However, in tumors, PepMV accumulated to 1.5 fold higher levels than PVX and tumors containing PepMV displayed more intense fluorescence than any other organs (e.g., tumor vs liver, $p<0.01$). The sequestration of nanoparticles including plant VNPs by the spleen and liver was anticipated and indicates clearance by the mononuclear phagocyte system (MPS). We previously observed the profound accumulation of PVX in the spleen (spleen>liver), but this appears to be unique to PVX and does not occur with other VNPs such as CPMV and TMV. Elongated nanoparticles are also expected to undergo renal clearance causing their accumulation in the kidneys because in spite of their length, such VNPs are only ~13 nm in diameter and can align with the blood flow to pass through the glomerular structure with a sub-20 nm size cutoff, followed by absorption within the tubes as previously observed for PVX and synthetic particles such as carbon nanotubes.

Figure 5A:
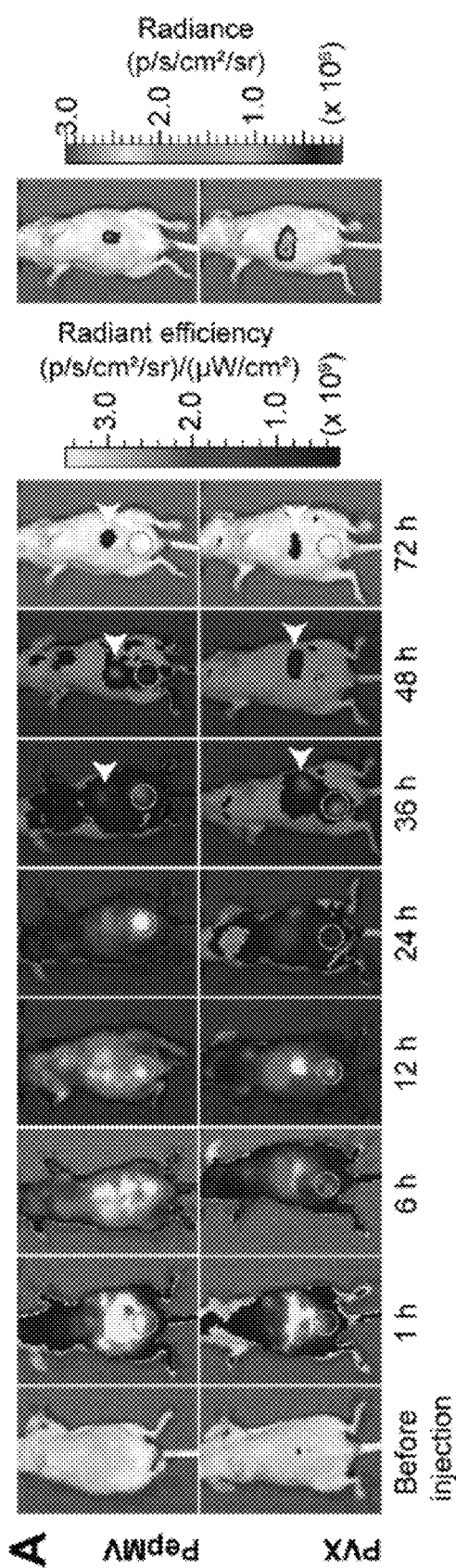
FIGS. 5(A-C) illustrate images and a graph showing biodistribution profiles of PepMV and PVX after intraperitoneal administration at a dose of 10 mg/kg in nu/nu mice bearing SKOV-3/Luc ovarian tumors. (A) Real time in vivo fluorescence images of PepMV and PVX over 72 h. Bladders are indicated by green circles. Tumors within the peritoneum were detected by in vivo bioluminescence imaging. The matched locations are indicated by white arrows in the fluorescence images. (B) Ex vivo fluorescence and luminescence images of excised organs from the mice injected with PepMV or PVX 72 h post administration. (C) Quantitative region of interest (ROI) analysis of each organ determined by total radiant efficiency per area. Data are expressed as means±SD (n=3).
Figure 5B:
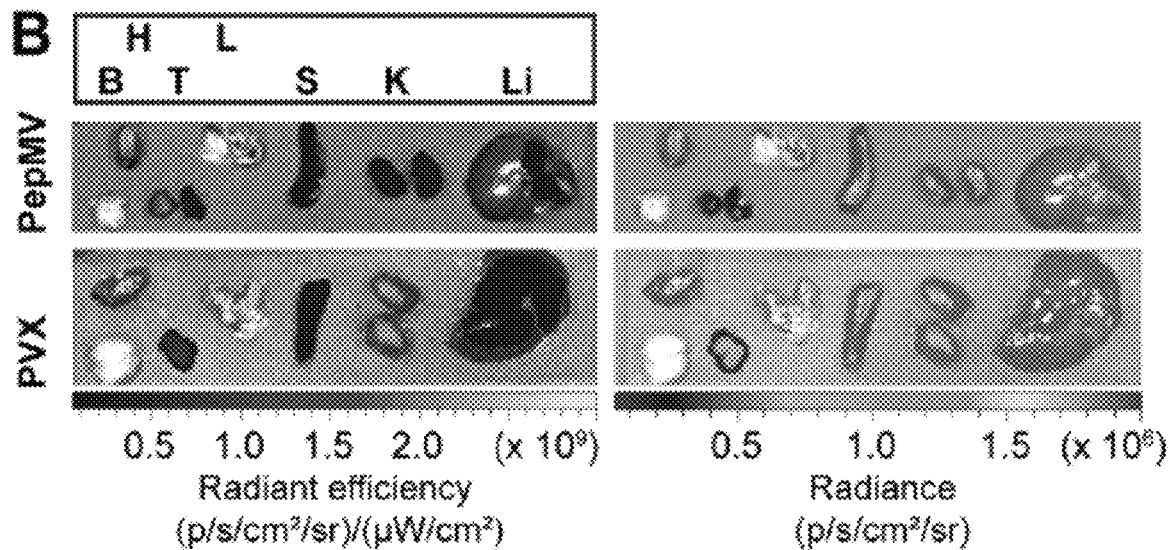
Figure 5C:
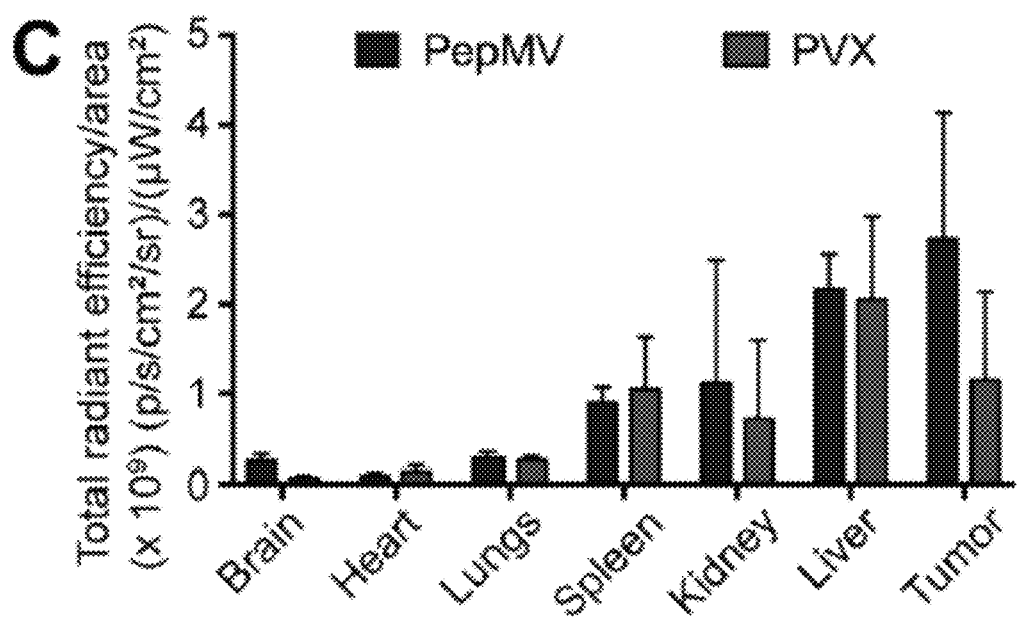

For the orthotopic ovarian cancer model, nu/nu mice were injected i.p. with luciferase-positive SKOV-3 cells ($2\times10^6$ cells) which are known to metastasize to the ovary, peritoneal wall, and diaphragm and form ascites fluid similar to human ovarian cancer. Luciferase-labeled cells were used to monitor disease progression within the peritoneal cavity. After 40 days, when the disease was established, PepMV-Cy5 or PVX-Cy5 particles (10 mg kg$^{-1}$ body weight) were administered into the i.p. space and images were captured using the IVIS system over the next 72 h (FIG. 5A). Although filamentous PepMV and PVX particles could be detected throughout the body (indicating systemic distribution following i.p. administration), the particles were concentrated at the highest levels in the peritoneum. Eventually, the VNPs were cleared from the body by renal clearance via the bladder (indicated by the strong fluorescence in the green circles, FIG. 5A). At 36 h post administration, when most PepMV and PVX had been removed from the body, tumor accumulation was indicated by the fluorescent signals from PepMV and PVX (indicated by white arrows) colocalizing with the luminescence of the tumor cells (FIG. 5A). Tumor retention was apparent for at least 72 h post administration (FIG. 5A). After 72 h, mice were euthanized for ex vivo imaging. FIG. 5B confirms the tumor homing of both VNPs, consistent with the in vivo imaging in FIG. 5A. Accumulation in organs of the reticuloendothelial system (spleen, liver and kidneys) was also observed (FIG. 5B). From ROI analysis, PVX and PepMV generated similar signals in the spleen, kidneys, and liver, with the latter accumulating the most particles in each case (FIG. 5C). There were no apparent differences between PepMV and PVX in these organs. It was interesting to note that in this mouse model, PVX is not preferentially sequestered in the spleen. Similar to the TNBC model, PepMV-treated animals showed double the fluorescence intensity in the tumor compared to that in animals treated with PVX.

Despite the differences in the tumor homing efficiency, both PepMV and PVX were found to accumulate in tumors, as previously reported for other nanoparticles with a high aspect ratio. This "passive" tumor homing after systemic administration can be explained by the enhanced permeability and retention (EPR) effect, a unique phenomenon in solid tumors, where tumor hypervascularization results in gaps between endothelial cells allowing the extravasation of nanoscale objects. The lack of lymphatic drainage leads to the retention of these materials. Rod-shaped and filamentous nanoparticles show enhanced tumor homing via EPR because they tend to evade phagocytosis and thus have prolonged circulation times, leading to more efficient tumor accumulation. In addition, the enhanced margination and better tissue penetration of elongated VNPs may also facilitate efficient extravasation to tumors. However, EPR-based delivery is significantly influenced by the tumor microenvironment and there is heterogeneity in the comparison of various tumor types, sizes, tissues of origin, primary vs metastatic sites, and/or patient conditions, resulting in case-to-case differences in the outcome of systemic administration. Local delivery via the i.p. route might offer an effective alternative strategy for the treatment of peritoneal malignancies. For example, in ovarian cancer, primary and metastatic tumors are frequently restricted to the peritoneal cavity, allowing direct exposure to treatments by i.p. injection. In addition, nanoparticle-based delivery prevents the rapid diffusion of small payloads into circulation systems following i.p. administration and thus enhances local drug concentrations (FIG. 5A), thus increasing tumor exposure and accumulation Here, the fluorescence of i.p. injected PepMV and PVX was confined within the i.p. space up to 72 h post administration, indicating slower clearance rates. The quantity of particles in ovarian tumors were an order of magnitude higher compared to VNP accumulation in the breast cancer model after i.v. delivery (24 h post administration) (FIGS. 4B and 5C). This indicates the effective tumor homing of elongated VNPs following i.p. administration targeting ovarian cancer.

Figure 1E:
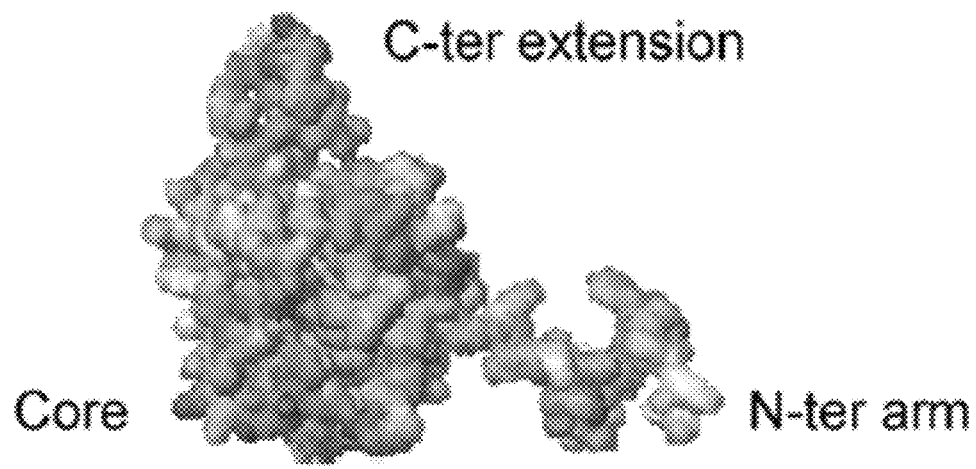
Figure 1F:
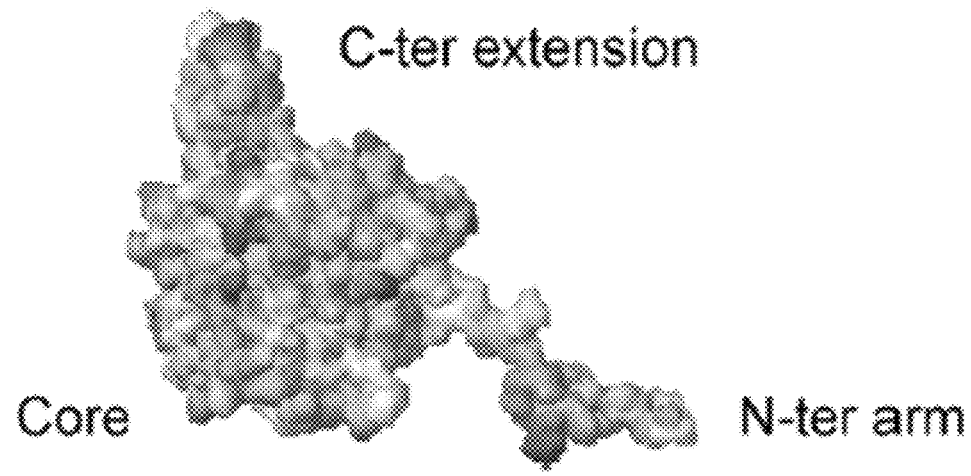

PepMV showed a 1.5-fold increase in tumor homing in the MDA-MB-231 mouse model compared to PVX and a 2-fold increase in the SKOV-3 model (FIGS. 4B and 5C). The biodistribution and tumor homing properties of PepMV and PVX may differ because of their surface charges, surface hydrophilicity/hydrophobicity, and protein—protein interactions. The surface electrostatic potential of PepMV and PVX was estimated in silico using the Bluues server based on the generalized Born model. Overall, the assembled PepMV and PVX CPs have negatively charged surfaces (FIGS. 1E, F). However, the protein corona, here defined as the outermost protein layer that would interface with the biological milieu, comprises the first 20 amino acid residues of each CP, which is flexible and exposed to the solvent. This is not shown in the model due to the lack of electron density, reflecting its flexible and disordered state. When we consider these flexible arms, structural differences can be detected, which may explain the differences observed in vivo. The PepMV sequence (PDB 5FN1) contains two negatively charged aspartic acid residues (Asp 3 and Asp 19) and the positively charged Lys 18, whereas PVX (NCBI AAV27212.1) contains only one charged amino acid: Lys 20. Overall, the PepMV corona is slightly negative (~1.2) whereas the PVX corona is slightly positive (0.8) at pH 7.4 as determined using the Protein Calculator tool. Regarding the hydrophobic nature of these peptide tails, PepMV has a GRAVY score of −0.33 compared to −0.45 for PVX, indicating that both peptide tails are hydrophilic. However, the hydropathy plots indicate that the outermost N-terminal portion of PepMV is hydrophilic whereas the equivalent part of PVX is hydrophobic. These differences may influence the opsonization on the nanoparticles in which hydrophobic surfaces are more prone to protein adsorption for clearance by the reticuloendothelial system. Furthermore, the amino acid compositions of PepMV and PVX are distinct and these subtle differences in the surface chemistry may explain the enhanced tumor homing of PepMV compared to PVX. Future work is required to systematically investigate the structure—function relationship between the charge, hydrophobicity, and/or protein composition of plant VNPs, because these properties can be tuned by surface modification, e.g., by chemical conjugation using polyethylene glycol or zwitterionic polymers or by genetic engineering to tailor the amino acid sequences.

Here PepMV is shown to be an effective nanoparticle platform for drug delivery and bioimaging applications. PepMV was found to have multiple surface-exposed Lys residues, and a bioconjugation procedure for the addition of dyes and other molecules via amine-NHS coupling has been established, allowing the preparation of a high-payload nanoplatform. PepMV can carry up to 1600 chemical modifiers per particle. In mouse models of TNBC and ovarian cancer, up to twice as much PepMV accumulated within the tumor compared to PVX, indicating better tumor homing despite the similar size and shape.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of targeting cancer tissue in a subject, comprising administering to the subject a pepino mosaic virus (PepMV) carrier comprising a PepMV particle modified to carry an imaging agent or a cytotoxic compound,
    wherein the PepMV carrier targets cancer tissue selected from the group consisting of triple negative breast cancer (TNBC) tissue or ovarian cancer tissue and has increased tumor homing to triple negative breast cancer (TNBC) tissue and to ovarian cancer tissue compared to a potato virus X (PVX) carrier,
    wherein the PepMV carrier is administered via systemic or intraperitoneal (i.p.) administration, and
    wherein the PepMV carrier has 1.5-fold increase in tumor homing in triple negative breast cancer (TNBC) tumors and 2-fold increase in tumor homing in ovarian cancer tumors compared to a potato virus X (PVX) carrier.

2. The method of claim 1, wherein the PepMV carrier has been PEGylated.

3. The method of claim 1, wherein the PepMV particle comprises an imaging agent.

4. The method of claim 3, wherein the imaging agent is a fluorescent molecule for fluorescent imaging.

5. The method of claim 4, wherein the imaging agent is Cy5.

6. The method of claim 3, wherein an effective amount of a PepMV carrier is administered, and further comprising the step of imaging cancer tissue in the subject using an imaging device subsequent to administering the PepMV carrier.

7. The method of claim 1, wherein the PepMV virus particle comprises an anti-cancer compound.

8. The method of claim 7, wherein the anti-cancer agent is an antitumor agent.

9. The method of claim 1, wherein the cancer tissue is triple negative breast cancer (TNBC) tissue.

10. A method of treating cancer in a subject identified as having cancer by administering to the subject a therapeutically effective amount of a pepino mosaic virus (PepMV) carrier comprising a PepMV particle modified to carry an anticancer agent,
    wherein the PepMV carrier targets cancer tissue selected from the group consisting of ovarian cancer or triple negative breast cancer (TNBC) and has increased tumor homing to triple negative breast cancer (TNBC) tumors and to ovarian cancer tumors compared to a potato virus X (PVX) carrier,
    wherein the PepMV carrier is administered via systemic or intraperitoneal (i.p.) administration, and
    wherein the PepMV carrier has 1.5-fold increase in tumor homing in triple negative breast cancer (TNBC) tumors and 2-fold increase in tumor homing in ovarian cancer tumors compared to a potato virus X (PVX) carrier.

11. The method of claim 10, wherein the PepMV carrier has been PEGylated.

12. The method of claim 10, wherein the anticancer agent is an antitumor agent.

13. The method of claim 10, wherein the cancer is triple negative breast cancer (TNBC).

14. The method of claim 10, wherein the PepMV carrier is administered together with a pharmaceutically acceptable carrier.

* * * * *